(12) United States Patent
Boguslavsky et al.

(10) Patent No.: US 9,911,573 B2
(45) Date of Patent: Mar. 6, 2018

(54) METHODS, APPARATUSES, SYSTEMS AND SOFTWARE FOR TREATMENT OF A SPECIMEN BY ION-MILLING

(71) Applicants: Dimitry Boguslavsky, Haifa (IL); Mark Kovler, Maple (CA)

(72) Inventors: Dimitry Boguslavsky, Haifa (IL); Mark Kovler, Maple (CA)

(73) Assignee: IB Labs, Inc., Brooklyn, NY (US)

( * ) Notice: Subject to any disclaimer, the term of this patent is extended or adjusted under 35 U.S.C. 154(b) by 80 days.

(21) Appl. No.: 14/642,138

(22) Filed: Mar. 9, 2015

(65) Prior Publication Data

US 2015/0255248 A1 Sep. 10, 2015

Related U.S. Application Data

(60) Provisional application No. 61/950,109, filed on Mar. 9, 2014.

(51) Int. Cl.
| | |
|---|---|
| *C23C 16/50* | (2006.01) |
| *H01J 37/305* | (2006.01) |
| *G01N 1/32* | (2006.01) |
| *H01J 37/147* | (2006.01) |
| *H01J 37/20* | (2006.01) |

(52) U.S. Cl.
CPC ............ *H01J 37/3056* (2013.01); *G01N 1/32* (2013.01); *H01J 37/147* (2013.01); *H01J 37/20* (2013.01); *H01J 2237/0245* (2013.01); *H01J 2237/0827* (2013.01); *H01J 2237/1505* (2013.01); *H01J 2237/31745* (2013.01); *H01J 2237/31749* (2013.01)

(58) Field of Classification Search
CPC ............ H01J 2237/31745; H01J 2237/31749
USPC ...... 216/59, 65, 66; 156/345.4; 118/723 CB, 118/72 BFI
See application file for complete search history.

(56) References Cited

U.S. PATENT DOCUMENTS

| | | |
|---|---|---|
| 5,986,264 A | 11/1999 | Grunewald |
| 8,168,960 B2 | 5/2012 | Grunewald et al. |
| 2004/0121069 A1* | 6/2004 | Ferranti ............... G03F 1/74 427/140 |
| 2007/0184596 A1* | 8/2007 | Ando ............... H01L 21/68764 438/172 |

(Continued)

*Primary Examiner* — Binh X Tran
(74) *Attorney, Agent, or Firm* — Andrew D. Fortney; Central California IP Group, P.C.

(57) ABSTRACT

Methods, apparatuses, systems and software for ion beam milling or machining are disclosed. The apparatus includes a specimen holder, a table, one or more ion sources, rotatable ion optics, and an imaging device. The specimen holder is configured to hold a specimen in a stationary position during milling or machining. The table is configured to change the stationary position of the specimen holder in any of three orthogonal linear directions and an angular direction. The rotatable ion optics are configured to emit an ion beam towards a predetermined location on the specimen from any of the one or more ion sources at any angle around an axis that is orthogonal to a horizontal surface of the table when the angular direction of the table is 0°. The imaging device is configured to generate an image of the specimen including the predetermined location, thereby enabling real-time monitoring of the milling or machining process.

24 Claims, 34 Drawing Sheets

(56) References Cited

U.S. PATENT DOCUMENTS

| | | | | |
|---|---|---|---|---|
| 2008/0078750 | A1* | 4/2008 | Boguslaysky | H01J 37/147 219/121.41 |
| 2011/0203021 | A1* | 8/2011 | An | B82Y 15/00 850/58 |
| 2013/0180843 | A1* | 7/2013 | Boguslavsky | H01J 37/147 204/192.33 |
| 2013/0248354 | A1* | 9/2013 | Keady | H01J 37/3005 204/192.33 |
| 2013/0320209 | A1* | 12/2013 | Shichi | H01J 37/20 250/307 |
| 2015/0292077 | A1* | 10/2015 | Allain | B82Y 40/00 204/192.11 |

* cited by examiner

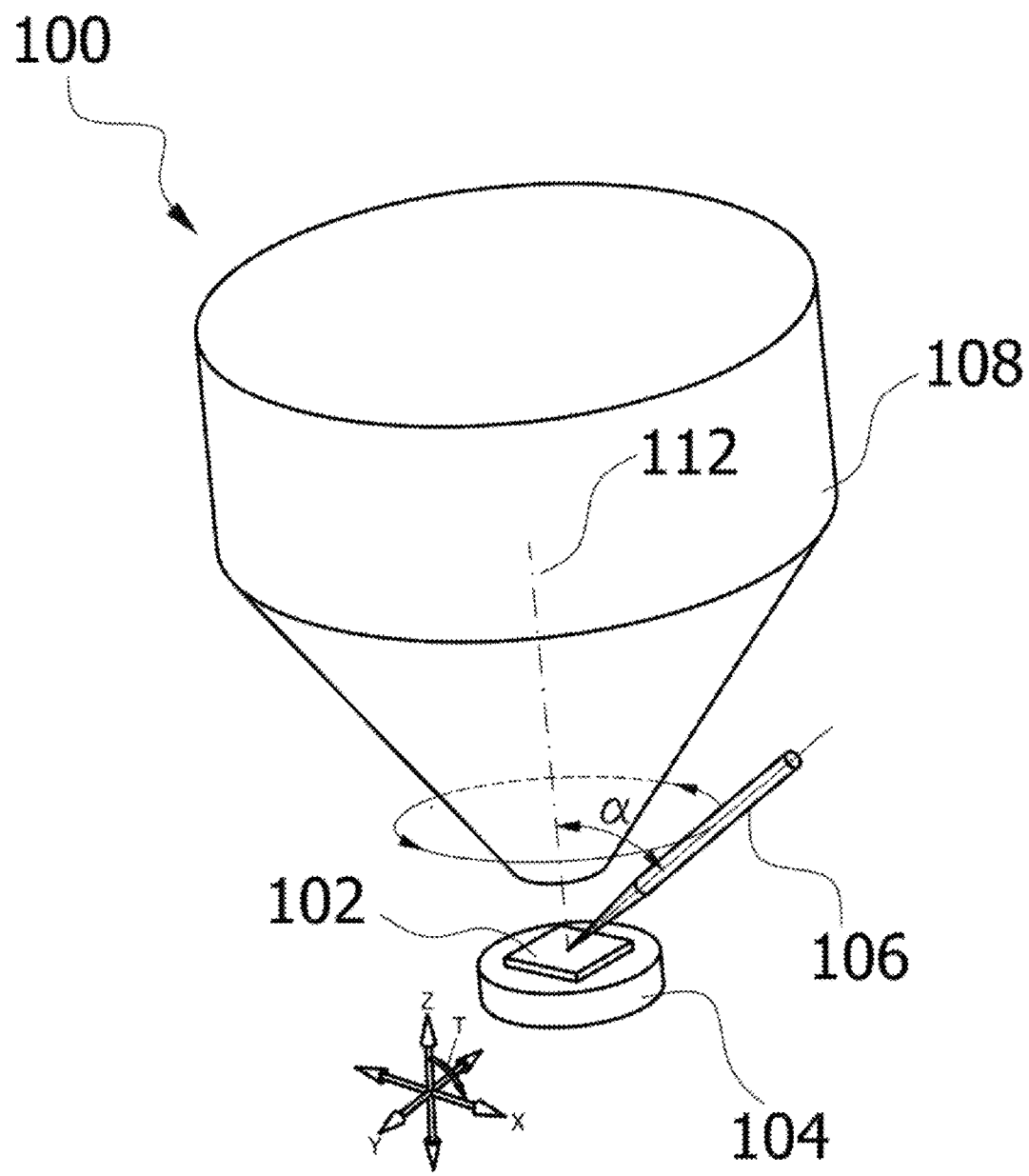

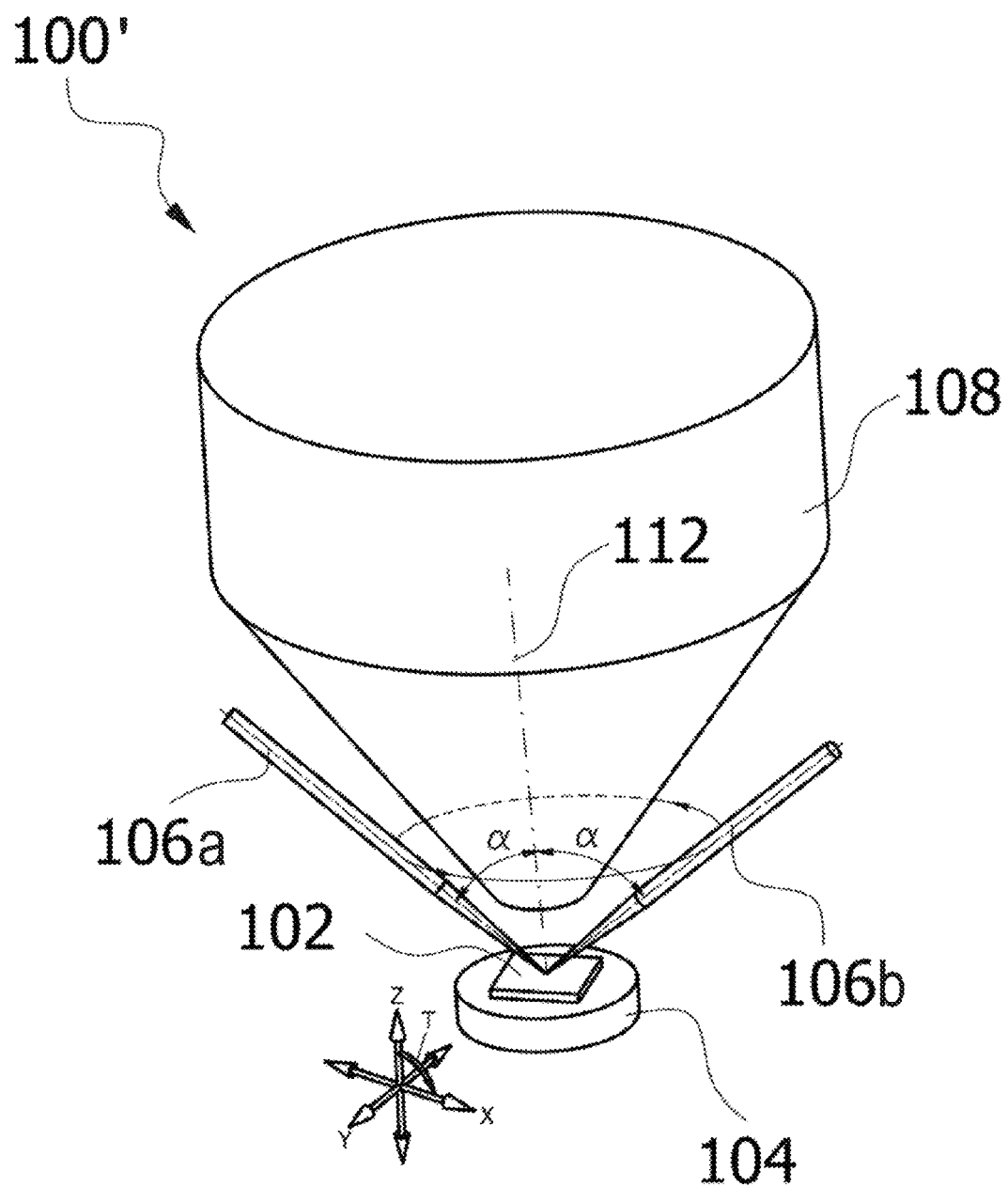

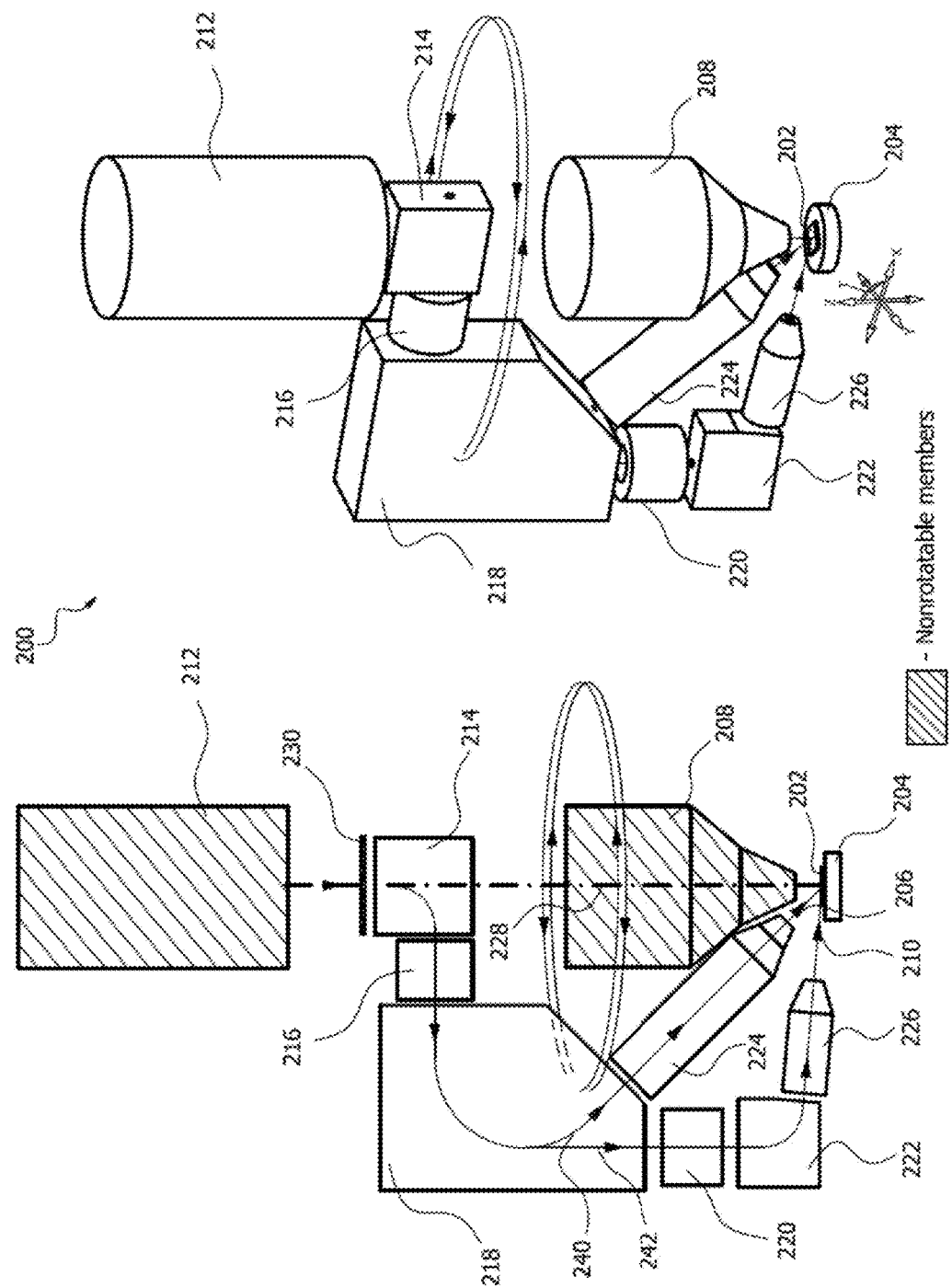

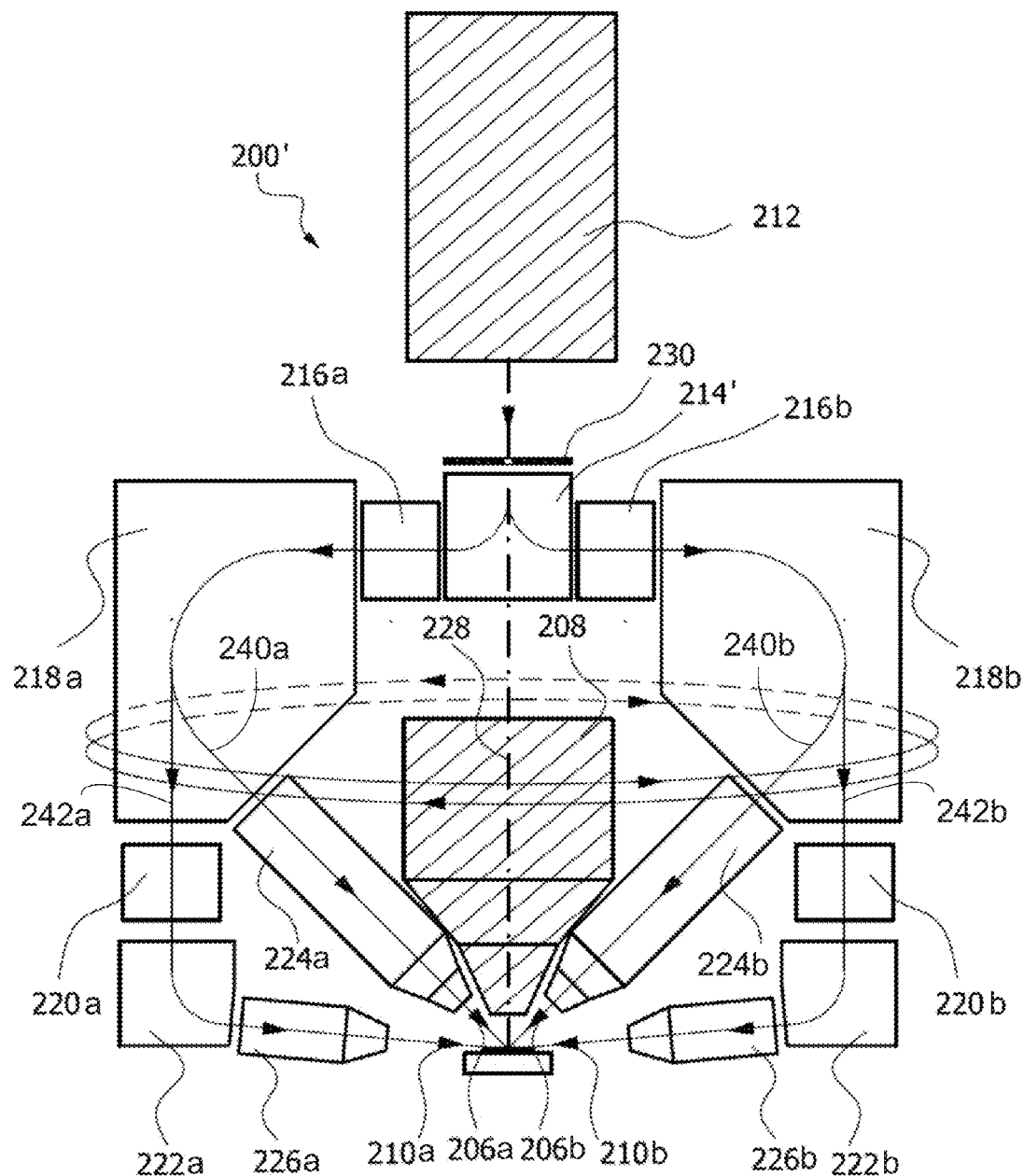

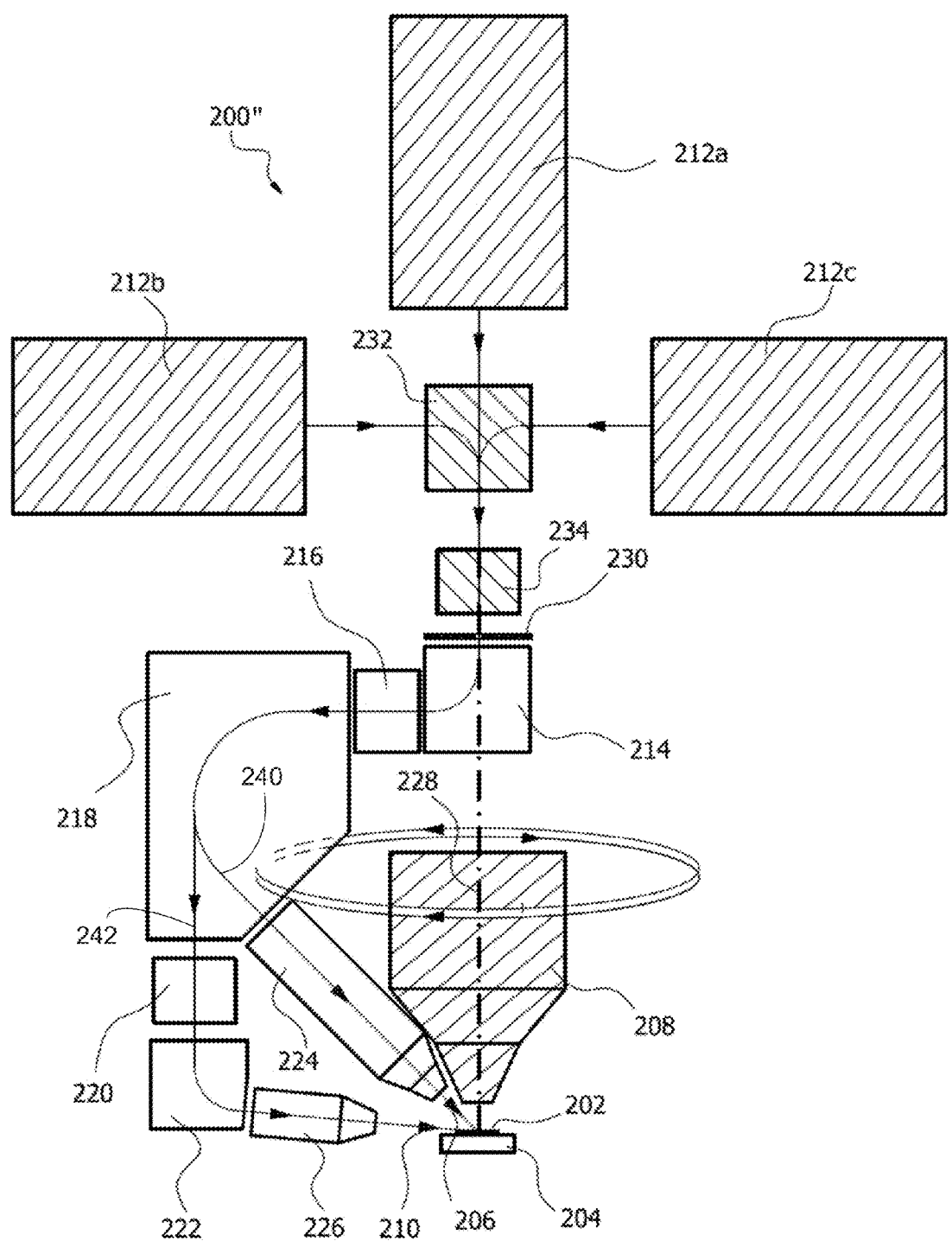

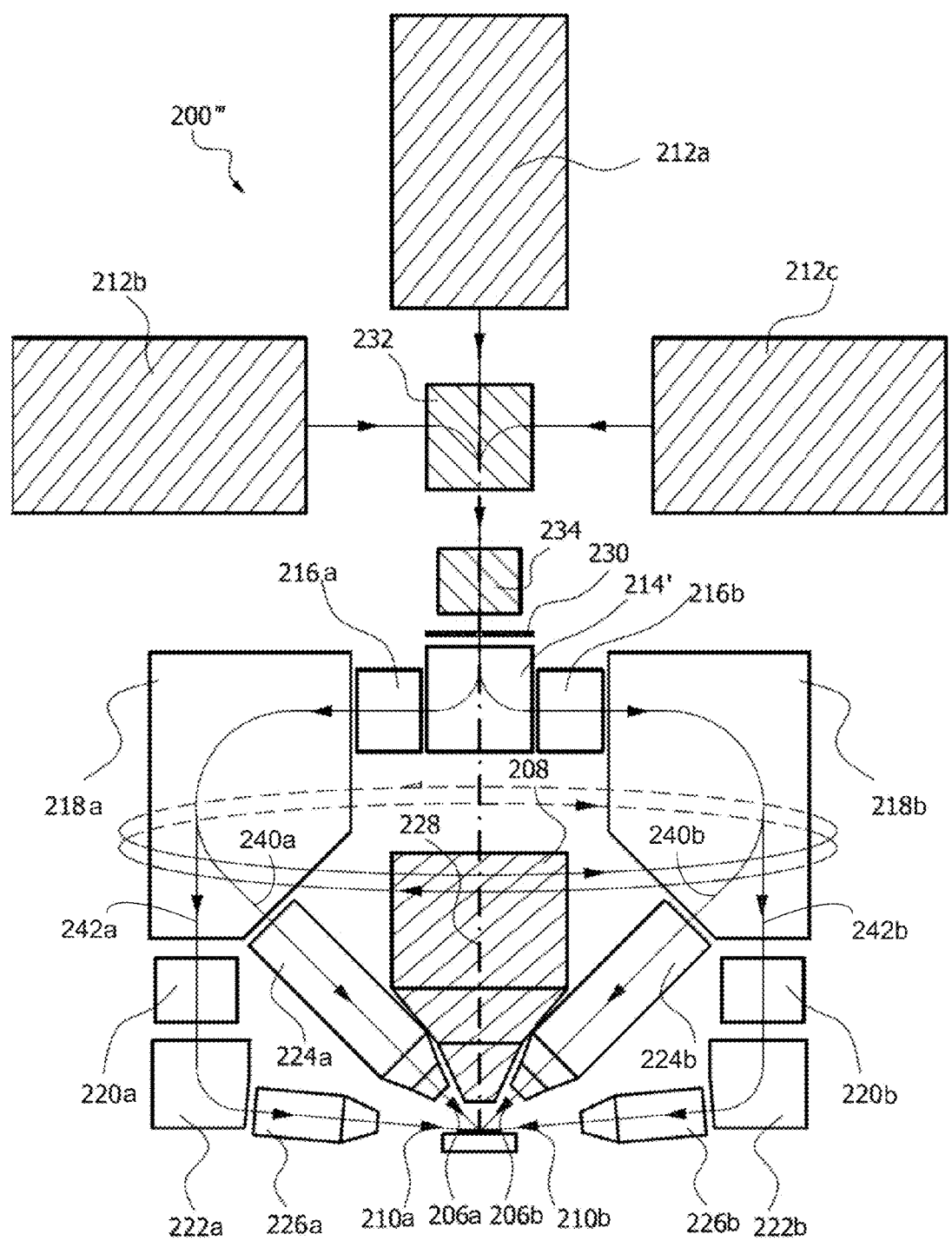

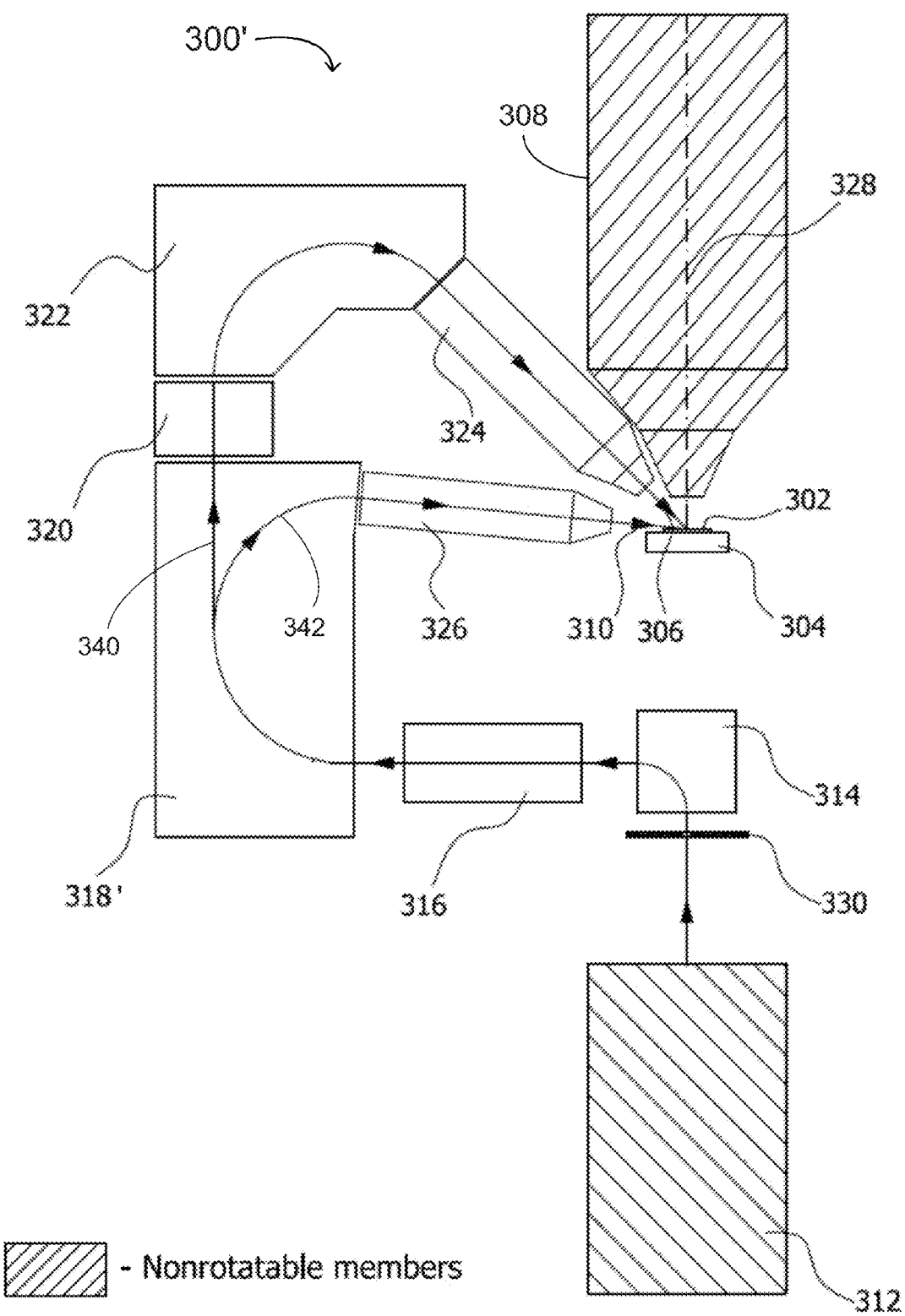

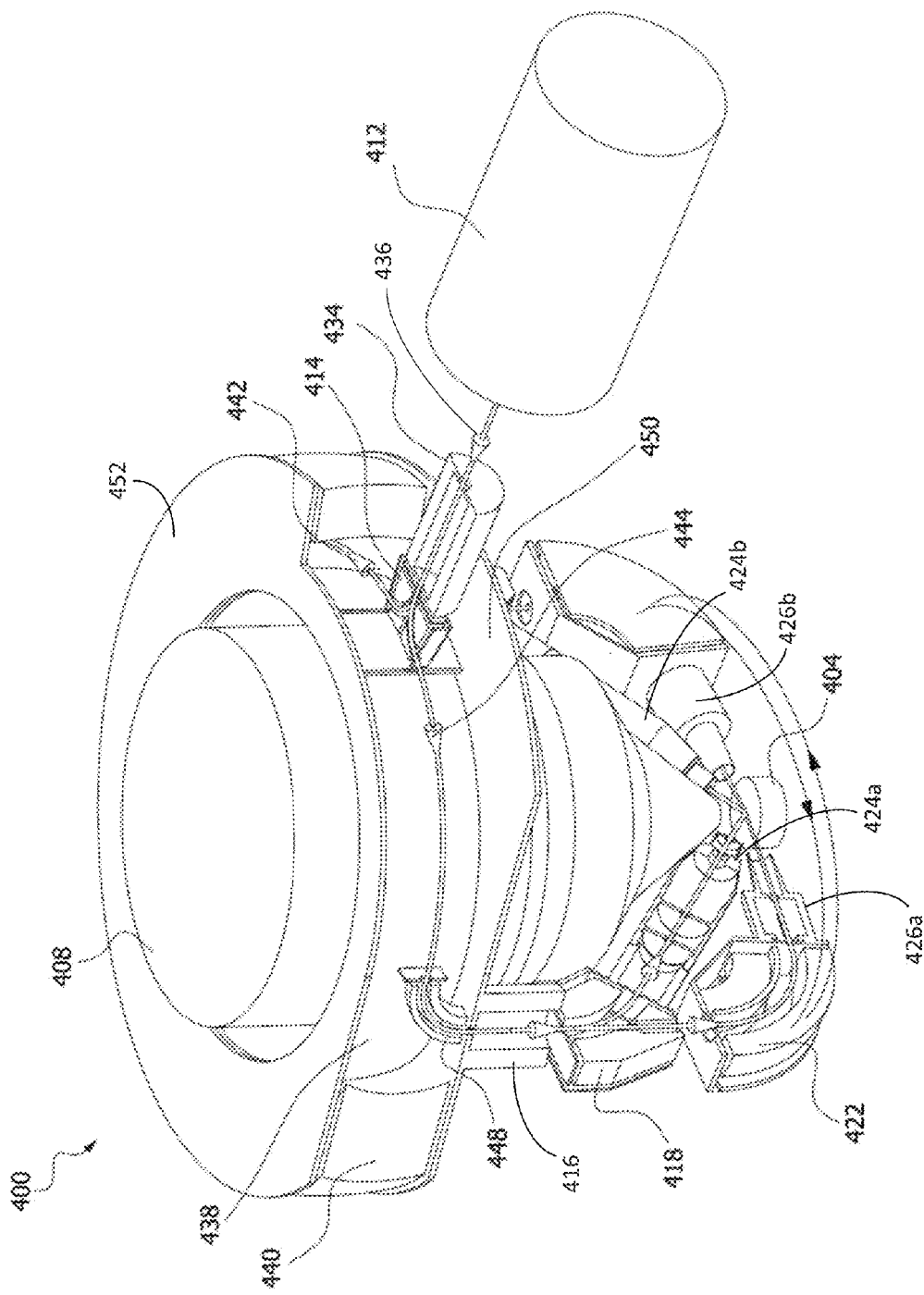

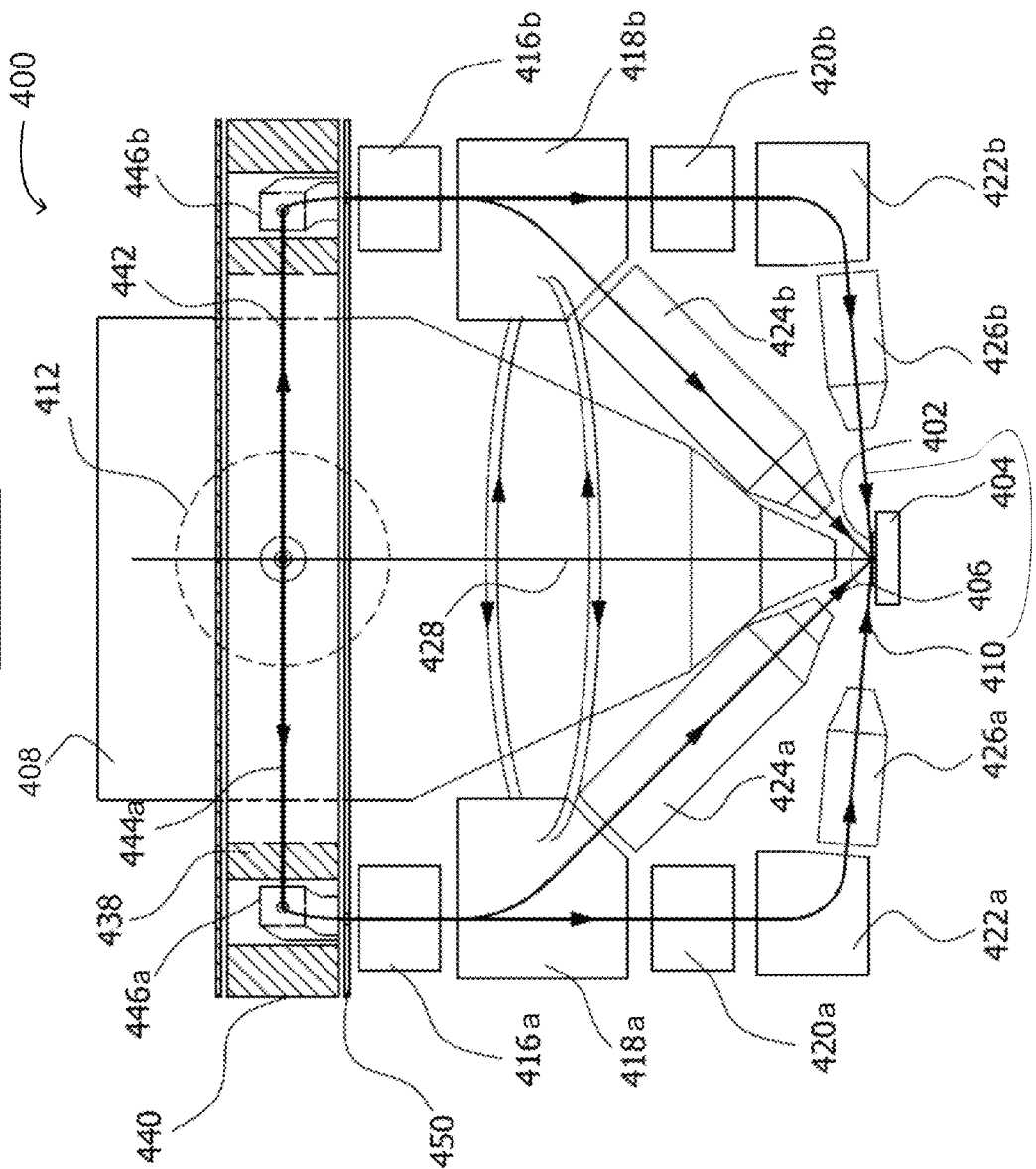

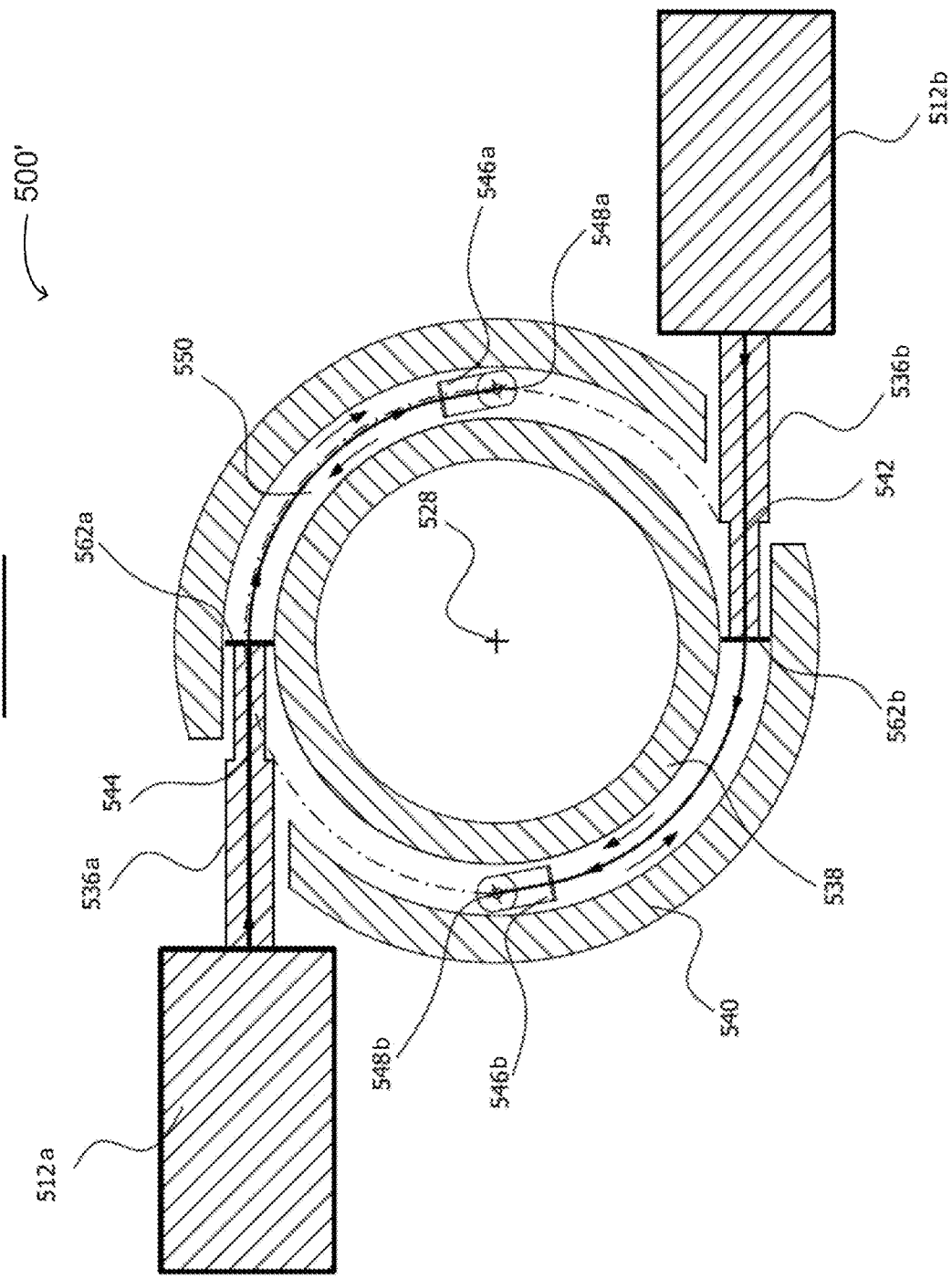

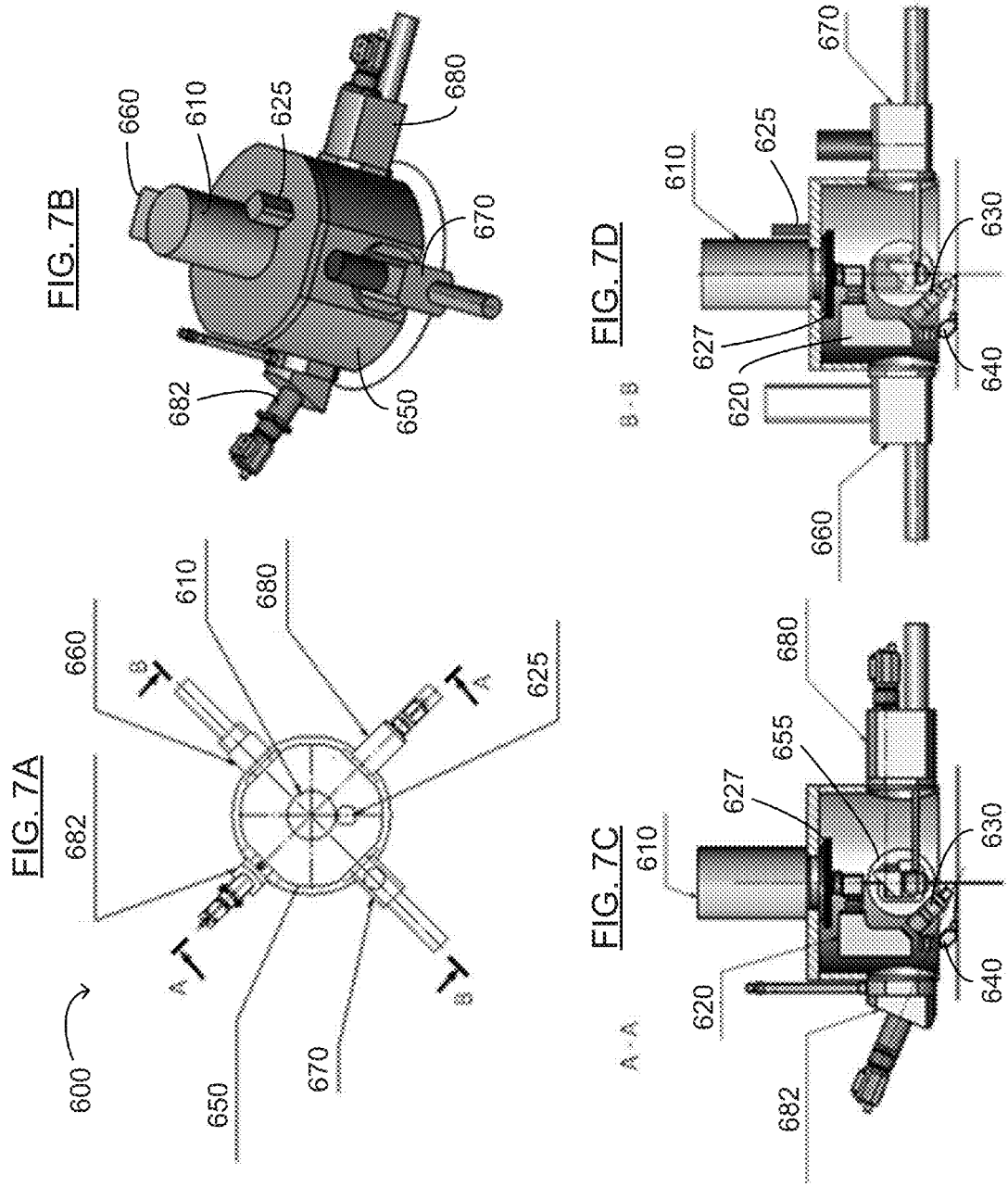

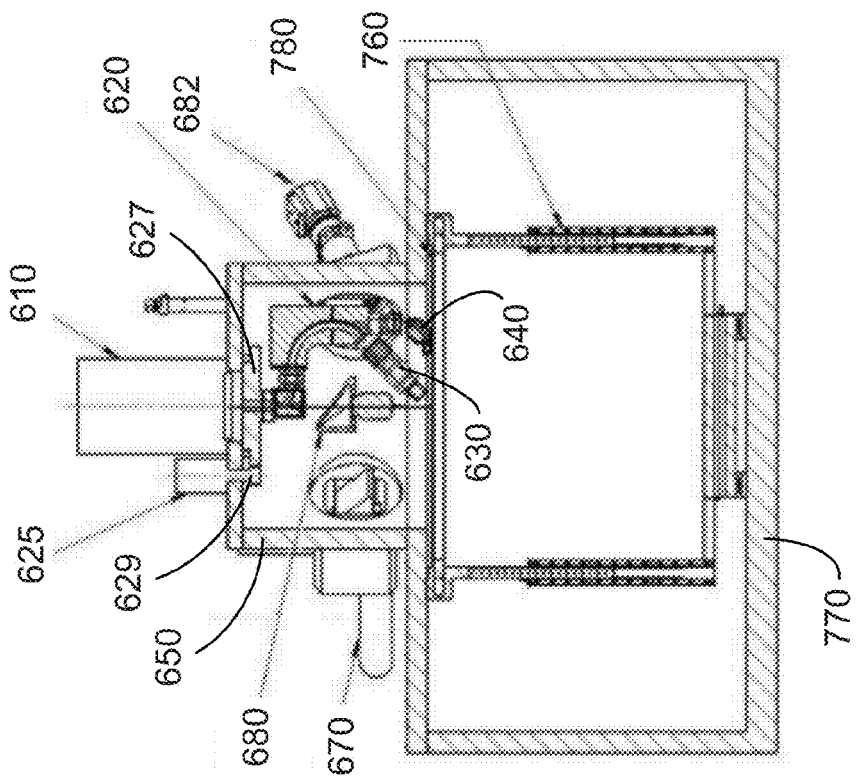
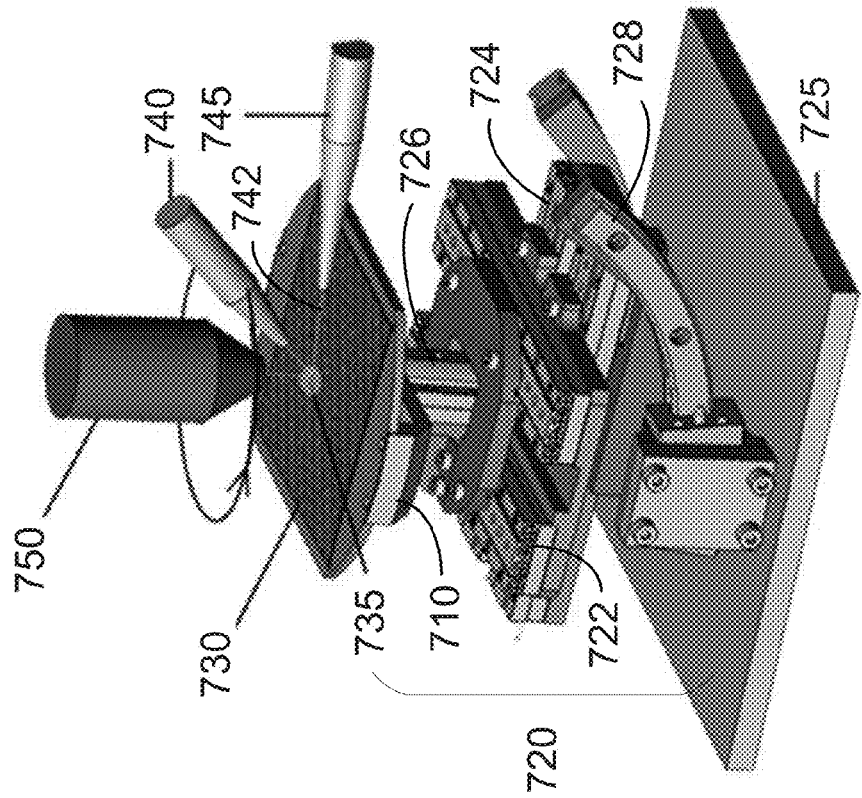

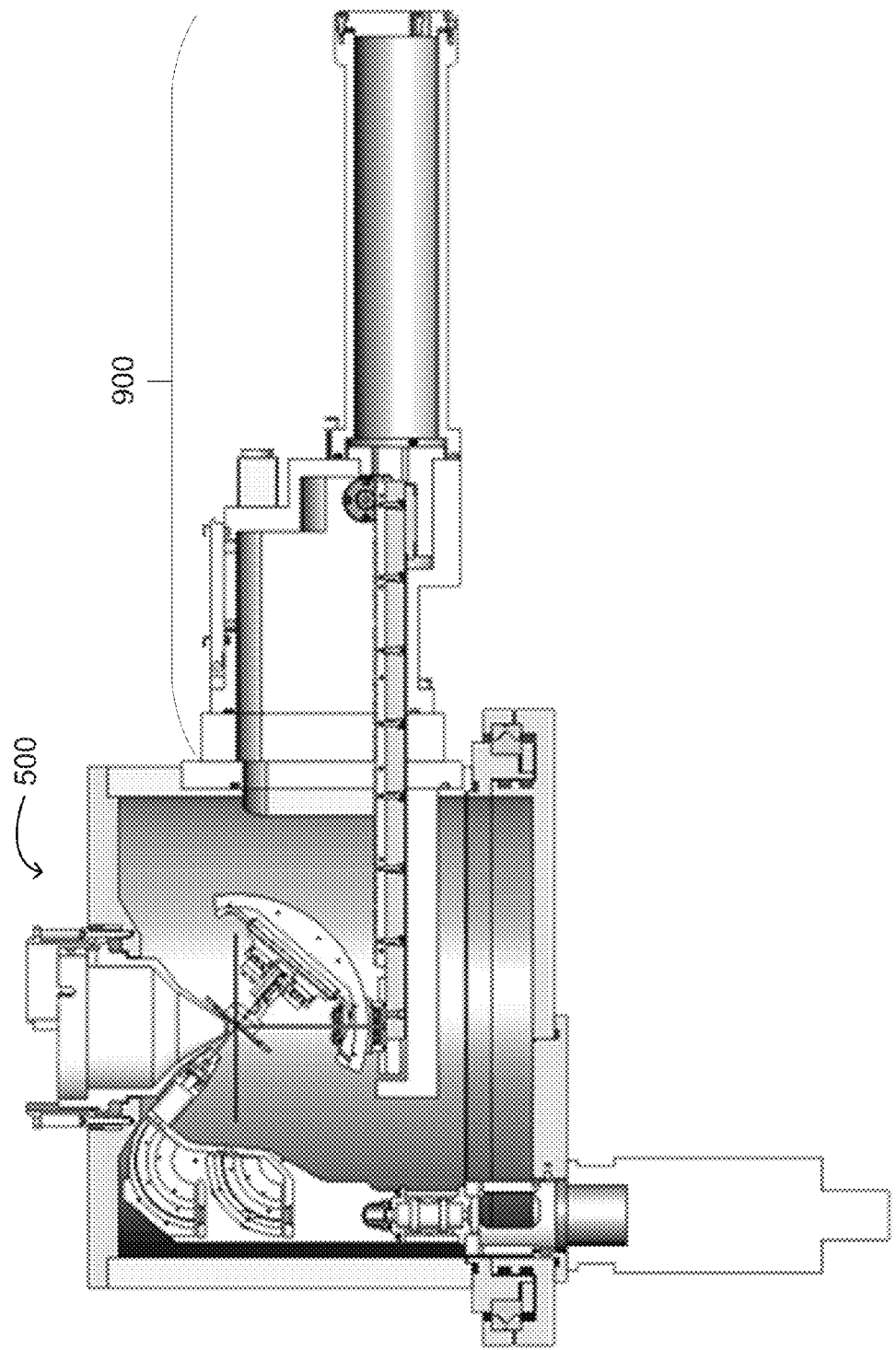

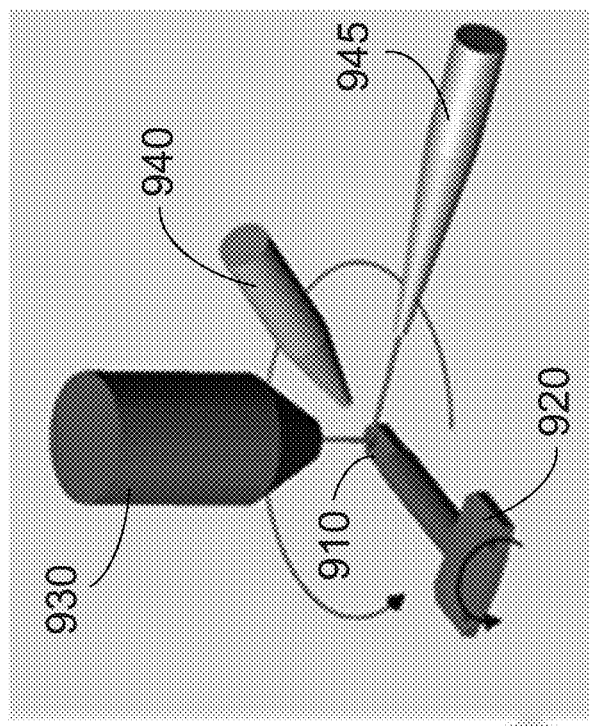
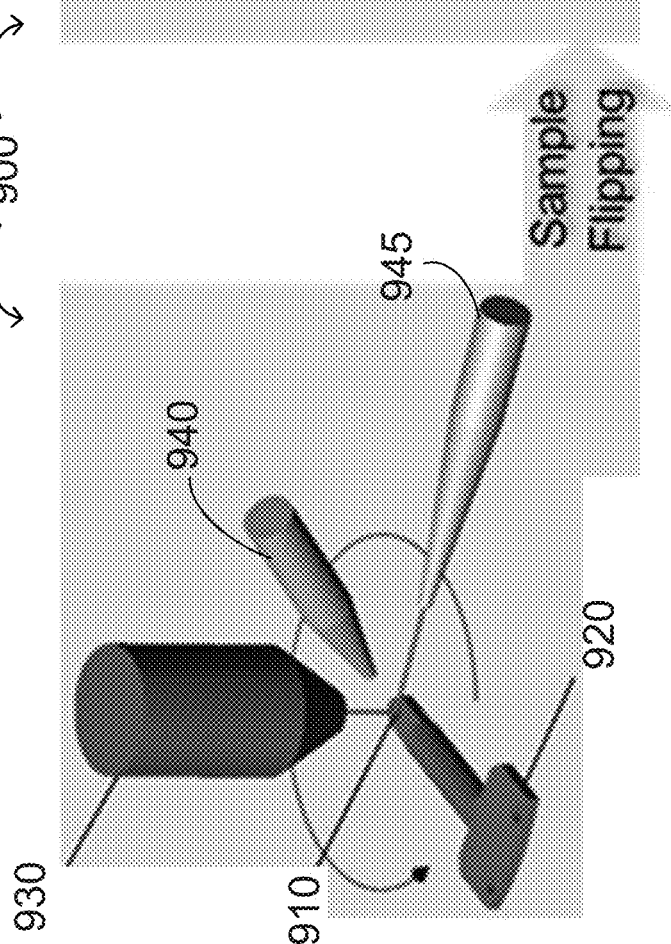
FIG. 15A
FIG. 15B

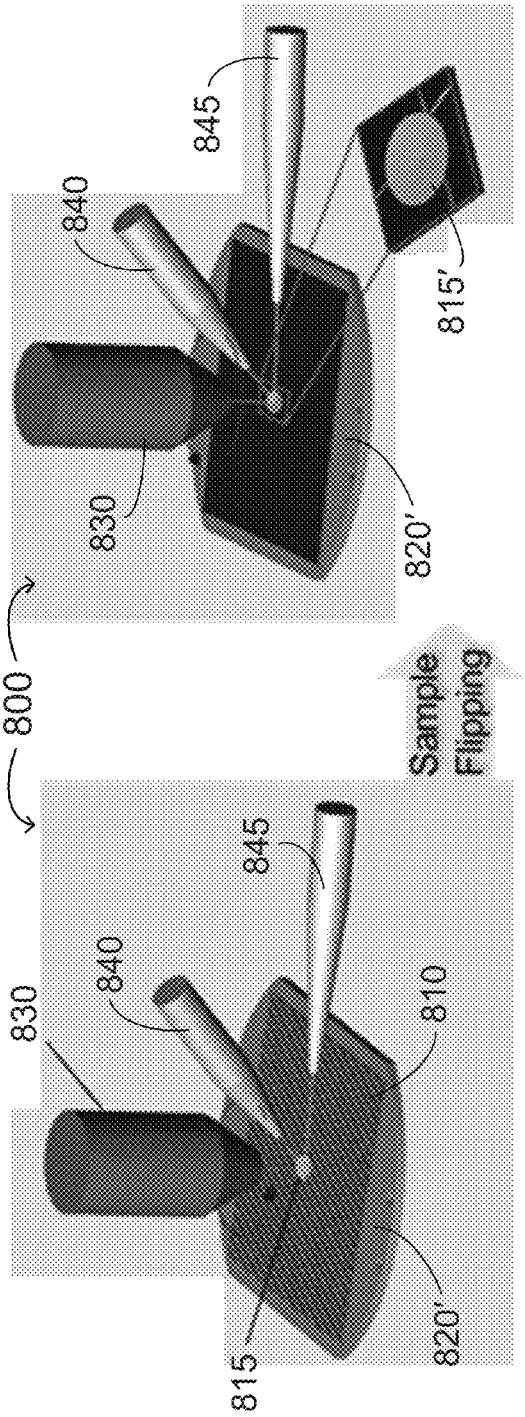
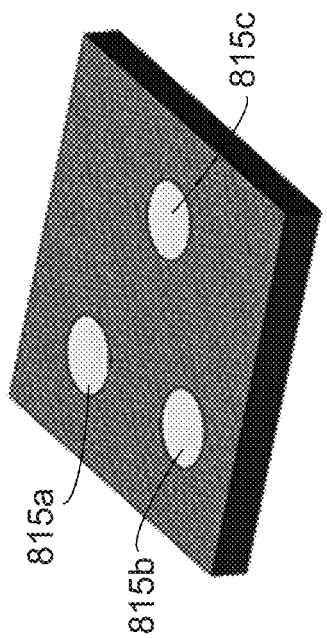
FIG. 16A  FIG. 16B  FIG. 16C

US 9,911,573 B2

METHODS, APPARATUSES, SYSTEMS AND SOFTWARE FOR TREATMENT OF A SPECIMEN BY ION-MILLING

RELATED APPLICATIONS

This application claims the benefit of U.S. Provisional Pat. Appl. No. 61/950,109, filed Mar. 9, 2014, pending, which is incorporated herein by reference in its entirety.

FIELD OF THE INVENTION

The present invention generally relates to the field of ion milling (e.g., surface and 3D treatment of specimen at atomic depth resolution by ion-milling), with and without laser beam assistance. More specifically, embodiments of the present invention pertain to methods, apparatuses, systems and software for ion milling a specimen that can be used in the fields of semiconductors, materials science, nanotechnology, and life science, among other fields.

DISCUSSION OF THE BACKGROUND

Conventionally, delayering methods in semiconductor and integrated circuit metrology and failure analysis include laborious, repetitive, and arguably blind polishing steps by general mechanical or RIE-polishing, followed by meticulous SEM inspection in between such steps. The average time for a single sample with an advanced minimum line width is on the order of 8-12 hours, meaning that at most, one machine can process 1 sample/day.

Various ion beam machining techniques are applicable to different end results. For example, a focused ion beam (FIB) can be used to cross-section a sample and/or to mill an area in the sample with nanometer-level precision. Beam currents in FIB tend to be in the range of 0.001-10 nA. FIB offers high beam precision and excellent target alignment capability. Plasma-FIB (PFIB) can be used for normal milling, and is applicable over a wide range of conditions. For example, PFIB can be used to mill a sample area on the order of 5-500 $\mu m^2$ using a beam having a current in the range of 1-1000 nA. Thus, the sputtering rate in PFIB is relatively high. However, FIB and PFIB techniques are generally insufficient for planar delayering for micromachining purposes, because of limitations in achieving nanometer scale roughness and planarity when treating different materials in the same sample.

Broad ion beam (BIB) techniques can be used for planar polishing and/or to mill a sample area on a millimeter scale. Beam currents in BIB tend to be in the range of 1000-20,000 nA. However, BIB generally lacks real-time control and site-specific (e.g., target alignment and beam precision) capabilities. Even more broadly, general polishing and RIE are inefficient, not site-specific, and generally require intermittent external microscope observations to determine progress.

No techniques are known to the inventors that provide site-specific planar delayering solutions at the wafer level. Thus, there is generally a lack of efficient, controlled and reliable site-specific delayering techniques and tools for advanced 45-10 nm nodes in semiconductor and/or integrated circuit metrology and/or failure analysis. A need is felt for such a technique and/or tool.

This "Discussion of the Background" section is provided for background information only. The statements in this "Discussion of the Background" are not an admission that the subject matter disclosed in this "Discussion of the Background" section constitutes prior art to the present disclosure, and no part of this "Discussion of the Background" section may be used as an admission that any part of this application, including this "Discussion of the Background" section, constitutes prior art to the present disclosure.

SUMMARY OF THE INVENTION

Embodiments of the present invention relate to methods, apparatuses, systems and software for micromachining, delayering, preparing and/or cleaning a sample. The apparatus or system generally comprises a specimen holder, a table, one or more ion sources, rotatable ion optics, and an imaging device. The specimen holder is generally configured to hold a specimen or sample in a stationary position. The table is generally configured to change the stationary position of the specimen holder in any of three orthogonal linear directions and an angular direction. The rotatable ion optics are generally configured to direct an ion beam towards a predetermined location on the specimen from any of the ion source(s) at any angle relative to a plane that is orthogonal to a horizontal surface of the table when the angle of table (i.e., in the angular direction) is 0°. The imaging device is generally configured to generate an image of the specimen, including the predetermined location.

In some embodiments, the table includes a first mechanism to move the sample holder in a lateral direction, a second mechanism to move the sample holder in a longitudinal direction, a third mechanism to move the sample holder in a vertical direction, and a fourth mechanism to move the sample holder in the angular direction. The angular direction may be defined by an axis in a plane defined by the lateral and longitudinal directions. In some embodiments, the sample holder (which may perform or conduct stage positioning of the specimen) may have more than four degrees of freedom.

When the apparatus or system includes more than one ion source, the ion sources include a first ion source and a second ion source different from the first ion source. For example, the first ion source may be a noble gas ion source, and the second ion source may be a Group 3, Group 4 or Group 5 ion source (where Group 3, Group 4 and Group 5 refer to Groups 3, 4 and 5 of the Periodic Table of the Elements). Alternatively or additionally, the first ion source may comprise a plasma ion source (for example, a duoplasmatron), and the second ion source may comprise a liquid metal or gas cluster ion source.

In various embodiments, the ion optics may comprise (i) a first ion path configured to direct or guide the ion beam at a first angle relative to an exposed surface of the specimen and (ii) a second ion path configured to direct or guide the ion beam at a second angle relative to the exposed surface of the specimen, where the first and second angles differ by at least 10°. In general, each of the first and second ion paths focus the ion beam onto the same (predetermined) location on the specimen. The ion optics may further comprise a first matching lens configured to focus the ion beam from the ion source(s), a bidirectional deflector configured to direct the ion beam to either the first ion path or the second ion path, a first deflector correcting the ion beam direction (e.g., as received from the ion source[s]), and/or a beam current monitor configured to determine a beam current of the ion beam. The first ion path may comprise a beam stigmator, an objective lens, and a beam scanning plate or beam scanning electrodes, and the second ion path may comprise a second matching lens, a second beam deflector, one or more beam shaping lenses, and a quadrupole beam aligner. The apparatus may further comprise a motor configured to rotate the ion optics.

In one configuration of the apparatus, the ion source(s) and the imaging device are on opposite sides of the specimen holder and the table. Alternatively, the ion source(s) and the imaging device may be on the same side of the specimen holder and the table.

In the apparatus, the imaging device may comprise an optical camera, a microscope (e.g., an optical microscope, a metallographic microscope, a laser microscope, or an electron microscope), and/or a thermo-vision device. The apparatus may further comprise a laser configured to irradiate the predetermined location with a predetermined dose of radiation and/or a laser interferometer configured to determine a depth of ion milling into the specimen at the predetermined location.

The method of use generally comprises generating an ion beam with an ion source, focusing the ion beam using rotatable ion optics, directing the ion beam along either of two paths in the rotatable ion optics at a predetermined location on a specimen in a stationary specimen holder, and generating an image of the specimen including the predetermined location using an imaging device. The two paths are at angles relative to an exposed surface of the specimen that differ by at least 10°. The ion beam may be generated by any of a plurality of ion sources operably connected or connectable to the rotatable ion optics.

In further embodiments, the method further comprises, prior to generating the ion beam, horizontally rotating the rotatable ion optics. Additionally or alternatively, the method may further comprise, prior to generating the ion beam, changing a position of the stationary specimen holder in any of three orthogonal linear directions and/or an angular direction. Prior to changing the position of the stationary specimen holder, the method may further comprise securing the specimen in the stationary specimen holder.

In some embodiments, the invention comprises software (e.g., a non-transitory computer-readable medium containing recorded or encoded instructions) which, when executed by a signal processing device configured to execute software, is configured to perform part or all of the method(s) discussed herein. For example, the invention may relate to a non-transitory computer-readable medium, comprising a set of instructions encoded thereon adapted to change a position of a stationary specimen holder in any of three orthogonal linear directions and/or an angular direction, horizontally rotate the rotatable ion optics, select one of the two paths to focus and direct the ion beam at the predetermined location on the specimen, generate the ion beam with an ion source, focus the ion beam onto the predetermined location on the specimen, and generate an image of the specimen including the predetermined location using an imaging device. In some embodiments, the rotatable ion optics are configured to direct an ion beam along either of two paths at a predetermined location on the specimen. The two paths are at angles relative to an exposed surface of the specimen that differ by at least 10°. In further embodiments, the set of instructions in the computer-readable medium may be further adapted to select one of a plurality of ion sources for generating the ion beam.

The present invention enables planar site-specific delayering at both chip and wafer levels, nanometer-level depth resolution, increased speeds (e.g., order-of-magnitude) relative to existing methods, real-time process control, end-point detection and automation, and ability to integrate with existing analytical techniques. The present apparatus and/or system spans applications ranging from focused ion beam (FIB) to broad ion beam (BIB), and enables in situ ion beam milling and imaging. The present micro-machining apparatus, system and method provide a convenient platform for failure analysis and 3D metrology in fields from microelectronics to materials science (e.g., for layer-by-layer materials analysis, or chemical composition and contamination analysis when combined with analytical tools) to life sciences. The present apparatus and system are amenable to an open-concept modular design, and are configurable as a stand-alone instrument or integratable into existing scanning electron microscopes, FIBs, mass spectrometers, Raman spectrometers, and other analytical tools.

The present system and/or apparatus, which may be referred to herein as a "Universal Ion Beam (UIB)" machining system, is designed for site-specific planar polishing and micromachining, among other functions and applications. The inventive process is optimized for in situ delayering, sample preparation for scanning election microscopy (SEM) and tunneling election microscopy (TEM), and/or post-FIB final cleaning. The present system, apparatus, and method provide high quality processing and results. For example, curtaining, amorphization and other ion-induced artifacts (e.g., by gallium or other relatively heavy ions) can be minimized or eliminated. The present system, apparatus, and method can also provide excellent process accuracy. For example, the process, including endpoint monitoring, can be provided by high-resolution/high-sensitivity imaging and/or analytical optical or electronic signal control (e.g., for surface analysis). Examples of such imaging and/or analytical optical/electronic signal control techniques include interferometry, spectroscopic reflectometry, electron back-scattering, mass spectrometry, XPS, Auger spectroscopy, etc. The present system, apparatus, and method provide relatively high throughput. For example, 4-10 TEM/STEM samples per 8-12 hour period (e.g., a typical work shift in a failure analysis lab) can be processed using the present invention. The present system, apparatus, and method are applicable to a variety of applications and sample preparation modes. Automated control of process accuracy, quality and termination can also be achieved by the present system, apparatus, and method.

Major features of the present ion milling apparatus include substantially unlimited beam positioning and maneuvering over a stationary sample, which enables true real time process control during substantially the entire course of ion milling (enabled by the stationary sample), high quality planar milling (enabled by the azimuthal beam and maneuverability thereof), sputtering rate control (enabled by the variable incidence angle of the ion beams), and a wide range of beam sizes from focused (tens of nm) to broad (mm range) enabled by the beam optics. The design and/or architecture of the present apparatus enables use of a combination of swappable ion sources in a single machine for best choice of the ion for a particular milling application (e.g., a liquid metal ion beam can be used for high precision FIB, a xenon or argon ion beam can be used for a high current beam, or one or more cluster gas ion beams can be used to provide atomic level surface smoothness of the sample).

These and other advantages of the present invention will become readily apparent from the detailed description of various embodiments below.

BRIEF DESCRIPTION OF THE DRAWINGS

FIGS. 1A-1B show components in exemplary rotatable ion beam systems over a stationary sample, including one or more ion beams at a predetermined angle with respect to an x-y plane of the sample holder and an imaging or analytical instrument.

FIGS. 4A-4D schematically illustrate exemplary rotatable unidirectional and bidirectional ion optical systems with one or more bottom mounted ion sources in accordance with the present invention.

FIGS. 5A-5C schematically illustrate an exemplary rotatable bidirectional ion optical system comprising a circular electrostatic condenser in accordance with embodiments of the present invention.

FIGS. 6A and 6B schematically illustrate exemplary ion beam injection mechanisms for rotatable ion optical systems comprising a circular electrostatic condenser in accordance with embodiments of the present invention.

FIGS. 7A-D respectively show a layout, chamber exterior/housing, and cross-sections of an exemplary apparatus/system in a topside configuration in accordance with one or more embodiments of the present invention.

FIG. 8A is a diagram showing an exemplary sample holder and table/manipulator in accordance with one or more embodiments of the present invention.

FIG. 8B is a diagram showing an exemplary, substantially complete system/apparatus with an exemplary alternative table/manipulator in accordance with one or more embodiments of the present invention.

FIG. 12A is a diagram showing the exemplary system and/or apparatus of FIG. 8A in a configuration for normal ion milling (i.e., a 90° configuration or setup) in accordance with one or more embodiments of the present invention.

FIGS. 15A-B respectively show front- and back-side milling using a reversible sample holder to prepare a sample for transmission electron microscopy (TEM) in accordance with one or more embodiments of the present invention.

FIGS. 16A-B respectively show grid-less SEM sample preparations for scanning transmission electron microscopy (STEM) imaging by sequential front and back side milling of a sample to TEM thickness in accordance with one or more embodiments of the present invention.

FIG. 16C shows a wafer or segment thereof with multiple site-specific grid-less electron transparent lamellas in accordance with one or more embodiments of the present invention.

DETAILED DESCRIPTION

Figure 2A:
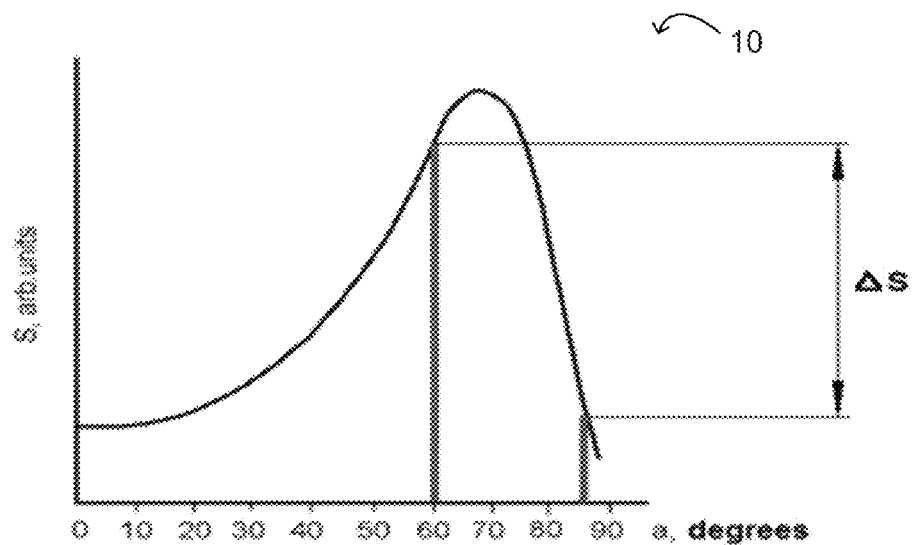
FIG. 2A is a graph showing sputtering (milling) yield as a function of beam angle.

Reference will now be made in detail to various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications and equivalents that may be included within the spirit and scope of the invention as defined by the appended claims. Furthermore, in the following detailed description, numerous specific details are set forth in order to provide a thorough understanding of the present invention. However, it will be readily apparent to one skilled in the art that the present invention may be practiced without these specific details. In other instances, well-known methods, procedures, components, and circuits have not been described in detail so as not to unnecessarily obscure aspects of the present invention.

Some portions of the detailed descriptions which follow are presented in terms of processes, procedures, logic or logic blocks, functions or functional blocks, processing, and other symbolic representations of operations on data bits, data streams or waveforms within a computer, processor, controller and/or memory. These descriptions and representations are generally used by those skilled in the data processing arts to effectively convey the substance of their work to others skilled in the art. A process, procedure, logic block, function, process, etc., is herein, and is generally, considered to be a self-consistent sequence of steps or instructions leading to a desired and/or expected result. The steps generally include physical manipulations of physical quantities. Usually, though not necessarily, these quantities take the form of electrical, magnetic, optical, or quantum signals capable of being stored, transferred, combined, compared, and otherwise manipulated in a computer or data processing system. It has proven convenient at times, principally for reasons of common usage, to refer to these signals as bits, waves, waveforms, streams, values, elements, symbols, characters, terms, numbers, information, or the like.

It should be borne in mind, however, that all of these and similar terms are associated with the appropriate physical quantities and are merely convenient labels applied to these quantities. Unless specifically stated otherwise and/or as is apparent from the following discussions, it is appreciated that throughout the present application, discussions utilizing terms such as "processing," "operating," "computing," "calculating," "determining," "transforming," "displaying" or the like, may refer to the action and processes of a computer or signal processing system, or similar processing device (e.g., an electrical, optical, or quantum computing or processing device), that manipulates and transforms data represented as physical (e.g., electronic) quantities. The terms refer to actions and processes of the processing devices that manipulate or transform physical quantities within the component(s) of a system or architecture (e.g., registers, memories, flip-flops, other such information storage, transmission or display devices, etc.) into other data similarly represented as physical quantities within other components of the same or a different system or architecture.

Furthermore, for the sake of convenience and simplicity, the terms "specimen" and "sample" are generally used interchangeably herein, but are generally given their art-recognized meanings. Also, for convenience and simplicity, the terms "data," "data stream," "waveform" and "information" may be used interchangeably, as may the terms "connected to," "coupled with," "coupled to," and "in communication with" (each of which may refer to direct or indirect connections, couplings, and communications), but these terms are also generally given their art-recognized meanings.

A central feature of the system and/or architecture thereof is multi-directional beam maneuvering over a stationary sample. The system and/or architecture enables substantially unlimited beam positioning and maneuvering over a sample, and allows in-situ continuous ion-milling and imaging of the treated area, and true real-time control of the process quality and termination. In some embodiments, the present system comprises a combination of an ion source with rotatable ion optics, an optical microscope for sample observation (and thus real-time process control), a high accuracy nano-positioning manipulator for sample handling, and/or an optimized air-lock for rapid sample loading and vacuum readiness.

The sample can be globally and simultaneously accessed for both ion milling and imaging. A four degree-of-freedom X-Y-Z-tilt manipulator (e.g., table) enables precise target alignment and beam positioning, although the manipulator can have fewer degrees of freedom or more degrees of freedom. The ion milling process conducted by the present apparatus is facilitated by a wide choice of controlled ion beam shapes per given application. The system/apparatus design allows comprehensive customization and process add-ons.

The present apparatus is a technological system in a vacuum environment that combines (1) a static or stationary specimen, loaded into the system and positioned by a manipulator, (2) at least one ion source, (3) mechanically rotatable ion optics that shape and direct an ion beam toward the specimen at a number of controllable incident angles and that can rotate the beam around the area of interest on the specimen, (4) an optional laser interferometer that can control the process or influence the rate of material removal from the specimen surface in the area of interest, (5) an optional laser beam that radiates the specimen surface in the area of interest simultaneously with the ion beam to enhance selectivity of the ion milling and increase the sputtering rate, and (6) one or more imaging devices for visual control when positioning the area of interest on the specimen and during the course of the milling/polishing process. The invention, in its various aspects, will be explained in greater detail below with regard to exemplary embodiments.

Exemplary Components for a Rotatable Ion Beam System

FIGS. 1A-1B show components in exemplary rotatable ion beam systems over a stationary sample, including one or more ion beams at a predetermined angle with respect to an x-y plane of the sample holder and an imaging or analytical instrument (e.g., for surface characterization). The rotatable ion beam system 100 of FIG. 1A is a unidirectional, single beam system that comprises a precision sample stage 104 having at least four degrees of freedom (e.g., X, Y, Z, and angular tilt) that holds and positions a sample, target or specimen 102, a fine rotatable focused ion beam (FIB) 106 for machining purposes (e.g., precise cross-sectioning, cutting, hole drilling, etc.), and a surface imaging or analytical inspection device 108. The imaging or analytical inspection device 108 may comprise an optical microscope, laser confocal microscope, laser scanning microscope (LSM), mass spectrometer, or other surface-sensitive analytical instrument.

The fine rotatable FIB 106 is delivered at an effective (fast) ion milling incidence angle $\alpha$ in the range of 0°-70° relative to a normal surface (e.g., the uppermost horizontal surface of the precision sample stage 104 or the specimen 102 when the tilt angle is 0°). The rotatable FIB 106 can rotate 360° around the main rotating axis 112 of the system 100.

The precision sample stage 104 can move the specimen 102 in any of 3 orthogonal directions (i.e., along x, y and z axes as shown in FIG. 1A) and holds the 102 in a fixed or stationary position during ion milling. Advantages of the sample stage 104 holding the sample 102 in a stationary position include true real-time quality control (e.g., using the surface imaging or analytical inspection device 108). Advantages of the rotatable ion beam 106 and associated optics (not shown) include superior uniformity, planarity and roughness of the surface of the sample 102, and integration of the ion beam 106 with various imaging and surface-sensitive analytical instruments (e.g., surface imaging or analytical inspection device 108).

FIG. 1B shows a bidirectional, double beam rotatable ion beam system 100' that comprises the precision sample stage 104 that holds and positions the specimen 102, first and second fine rotatable FIBs 106a-b for machining purposes, and the surface imaging or analytical inspection device 108. The sample stage 104 and the imaging or analytical inspection device 108 may be the same as in FIG. 1A.

Ion beams 106a-b can be delivered independently from different ion sources, or delivered from different directions using different ion optical beam delivery units by switching or changing the directions of the beams (e.g., by rotating the beam 106a and/or the beam 106b around the axis 112 and/or by tilting the sample stage 104). A multi-beam guide (deflector; not shown in FIGS. 1A-B) with a beam switching function enables universality of the treatment of the sample 102 with different ion beams (e.g., using chemically inert ions such as $Ar^+$, $Xe^+$, etc.; chemically active atomic and molecular ions such as $O_2^+$, $SF_6^+$, $Cl^-$, $F^-$, $I^-$, $Br^-$, etc.; cluster ions, etc.) that are best suited for a given application in a single apparatus.

FIG. 2A is a graph showing sputtering (milling) yield as a function of beam angle. In general, a small grazing angle enables polishing by ion milling. In general, as the angle increases from small (e.g., 10° or less) to large (e.g., 60-70°), the amount of material removed during ion milling increases. From about 70° to about 90°, the yield decreases dramatically, but the focus may improve.

Figure 2B:
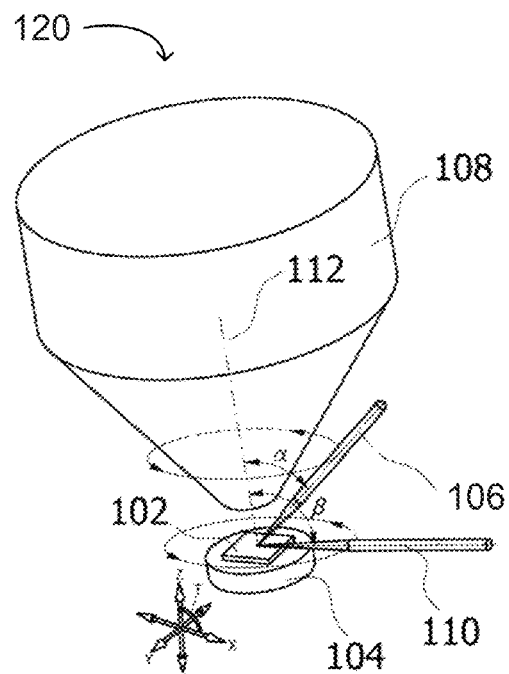
FIGS. 2B-D show components in exemplary rotatable ion beam systems over a stationary sample, including one or more double ion beam arrangements, each beam being at a predetermined angle with respect to an x-y plane of the sample holder, and an imaging or analytical instrument FIGS. 3A-3D schematically illustrate components for exemplary rotatable unidirectional and bidirectional ion optical systems with one or more top-mounted ion sources in accordance with the present invention.

FIG. 2B shows a unidirectional, double beam rotatable ion beam system 120 that comprises the precision sample stage 104 that holds and positions the specimen 102, fine rotatable FIB 106, rotatable grazing ion beam (GIB) 110, and the surface imaging or analytical inspection device 108. The sample stage 104, fine rotatable FIB 106, and the imaging or analytical inspection device 108 may be the same as in FIG. 1A. Grazing ion beam (GIB) 110 provides a surface machining function (e.g., polishing, gentle milling, etc.). The GIB 110 is delivered in a grazing (e.g., glancing) direction, which in many implementations refers to a direction of ≤10° with reference to the horizontal surface of the sample stage 104 or of the specimen 102 at 0°. The incidence angle β may be in the range of 75°-90° relative to a normal surface of the sample stage 104 set at 0°.

In some embodiments, ion beams 106 and 110 can be delivered independently from different ion sources. Alternatively, ion beams 106 and 110 can be delivered separately and/or independently by switching the ion beam path. A multi-beam guide (or deflector, not shown) with a beam switching function enables universality of treatment of the sample using different ion beams, one or more of which may be best suited for a given application in the apparatus 120 (e.g., chemically inert ions such as Ar, Xe, etc., chemically active atomic and molecular ions as described herein, cluster ions, etc.).

Figure 2C:
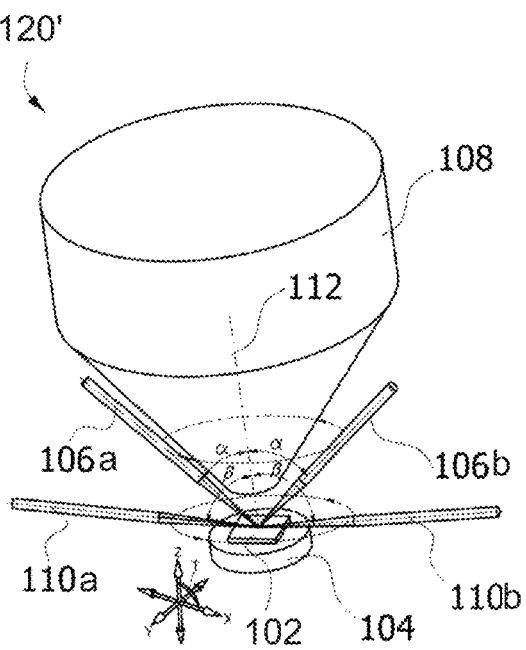

FIG. 2C shows a bidirectional, double beam rotatable ion beam system 120' that comprises the precision sample stage 104 that holds and positions the specimen 102, fine rotatable FIBs 106a-b, rotatable GIBs 110a-b, and the surface imaging or analytical inspection device 108. The sample stage 104 and the imaging or analytical inspection device 108 may be the same as in FIG. 1A, and the fine rotatable FIBs 106a-b and the rotatable GIBs 110a-b may be the same as ion beams 106 and 110 in FIG. 2B. Although the incidence angles α and β in FIG. 2C are the same in each of the two directions (i.e., from rotatable FIBs 106a-b and rotatable GIBs 110a-b, respectively), the angle α of the rotatable FIBs 106a and 106b may be different, and the angle β of the rotatable GIBs 110a and 110b may be different.

Grazing ion beams (GIBs) 110a-b provide a surface machining function (e.g., polishing, gentle milling, etc.). The GIBs 110a-b are delivered in a grazing (e.g., glancing) direction, which in many implementations refers to a direction of ≤10° with reference to the horizontal surface of the sample stage 104 at 0°. The incidence angle β may be in the range of 75°-90° relative to a normal surface of the sample stage 104 set at 0°.

Figure 2D:
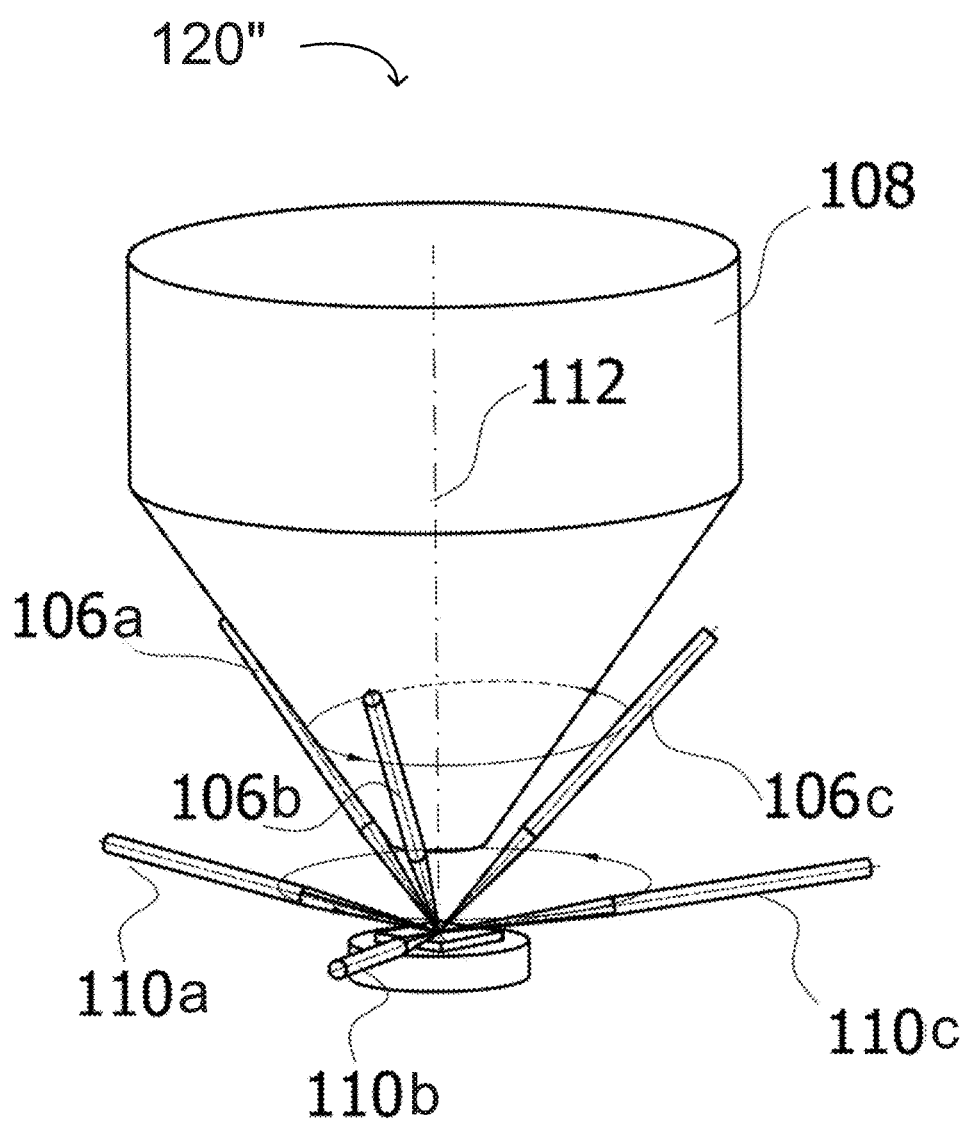

FIG. 2D shows a multi-directional, double beam rotatable ion beam system 120" that comprises the precision sample stage 104 that holds and positions the specimen 102, fine rotatable FIBs 106a-c, rotatable GIBs 110a-c, and the surface imaging or analytical inspection device 108. The sample stage 104 and the imaging or analytical inspection device 108 may be the same as in FIG. 1A, and the fine rotatable FIBs 106a-c and the rotatable GIBs 110a-c may be the same as ion beams 106 and 110 in FIG. 2B. The angles with which each pair 106a/110a, 106b/110b and 106c/110c of the fine rotatable FIBs and GIBs may be rotated around the axis 112 can be fixed or variable relative to each other, and variable with respect to a reference angle of 0° (which can be arbitrarily defined).

Exemplary "Topside" Rotatable Ion Beam Systems

FIGS. 3A-3D schematically illustrate exemplary rotatable unidirectional and bidirectional ion optical systems 200-200''' in accordance with the present invention. Components common to the optical systems 200-200''' include precision sample stage 204, surface imaging or analytical inspection device 208, and ion beam defining aperture 230. Non-rotatable components are designated with hatched lines. The precision sample stage 204 can move the specimen 202 in any of 3 orthogonal directions (i.e., along x, y and z axes as shown in FIG. 3A) and holds the specimen 202 in a fixed or stationary position during ion milling. The surface imaging or analytical inspection device 208 can be or comprise, e.g., an optical microscope, laser confocal microscope, laser scanning microscope (LSM), electron microscope, mass spectrometer, or other analytical instrument for analyzing the surface of the specimen 202. The stationary ion beam defining aperture 230 is arranged on and/or around the main rotational axis 228 of the system 200-200''', and provides a coaxial entrance of the ion beam from an ion source in the rotational stage of system 200-200'''.

FIG. 3A shows two views of an apparatus 200 that provides high-angle (aggressive milling) ion optics using a first ion beam path 240 and low-angle (gentle milling) ion optics using a second ion beam path 242 in accordance with one or more embodiments of the present invention. The apparatus 200 further includes an ion source 212, an ion beam deflector 214, an ion optical matching member 216, a bidirectional ion beam guide 218, a fine focused ion beam (FIB) module or member 224, an ion optical matching member 220, and an ion beam deflector 222. The ion source 212 can be any kind of ion source suitable for ion milling, surface machining, or other use of an ion beam. The ion beam deflector 214 may have one or more beam direction switching functions. The ion optical matching member 216 may comprise a matching lens or one or more beam correction electrodes. The fine focused ion beam (FIB) module or member 224 provides final focusing of the ion beam 206, shape correction of the ion beam 206, positioning of the beam 206 over the surface of the sample 202, and scanning of the ion beam 206 on the surface of the specimen 102. The ion optical matching member 220 may comprise a matching lens or beam correction electrodes. The ion beam deflector 222 guides the ion beam 210 in the grazing direction.

The choice of ion beam path 240 or 242 is based on the angular dependence of the sputtering yield (see, e.g., FIG. 2A). For example, a relatively high incident angle (e.g., >30°, and more preferably, from 45° to about 80°; see ion beam 206, which in one example is a fine focused ion beam [FIB]) of the beam trajectory is chosen for aggressive milling or cutting, and a glancing incident angle (e.g., <30°, and more preferably, ≤10°, but >0°; see ion beam 210, which can, in various embodiments, be a grazing ion beam [GIB] for surface machining) of the beam trajectory is chosen for gentle milling or polishing.

The bidirectional ion beam guide 218 is configured to redirect or switch the ion beam to either the first path 240 (e.g., for fast milling) or the second path 242 (e.g., for grazing milling). There are different control mechanisms and methods of changing of ion beam direction (e.g., beam deflection) using electrostatic or magnetic fields. Various configurations can be applied (e.g., cylindrical, spherical or toroidal condensers or deflectors, simple electrostatic system with double deflection plates, multi-electrode deflection systems, etc.). Spherical and toroidal deflectors provide stigmatic focusing of the ion beams that pass through them, and are preferable in a system for forming a FIB.

Figure 3E:
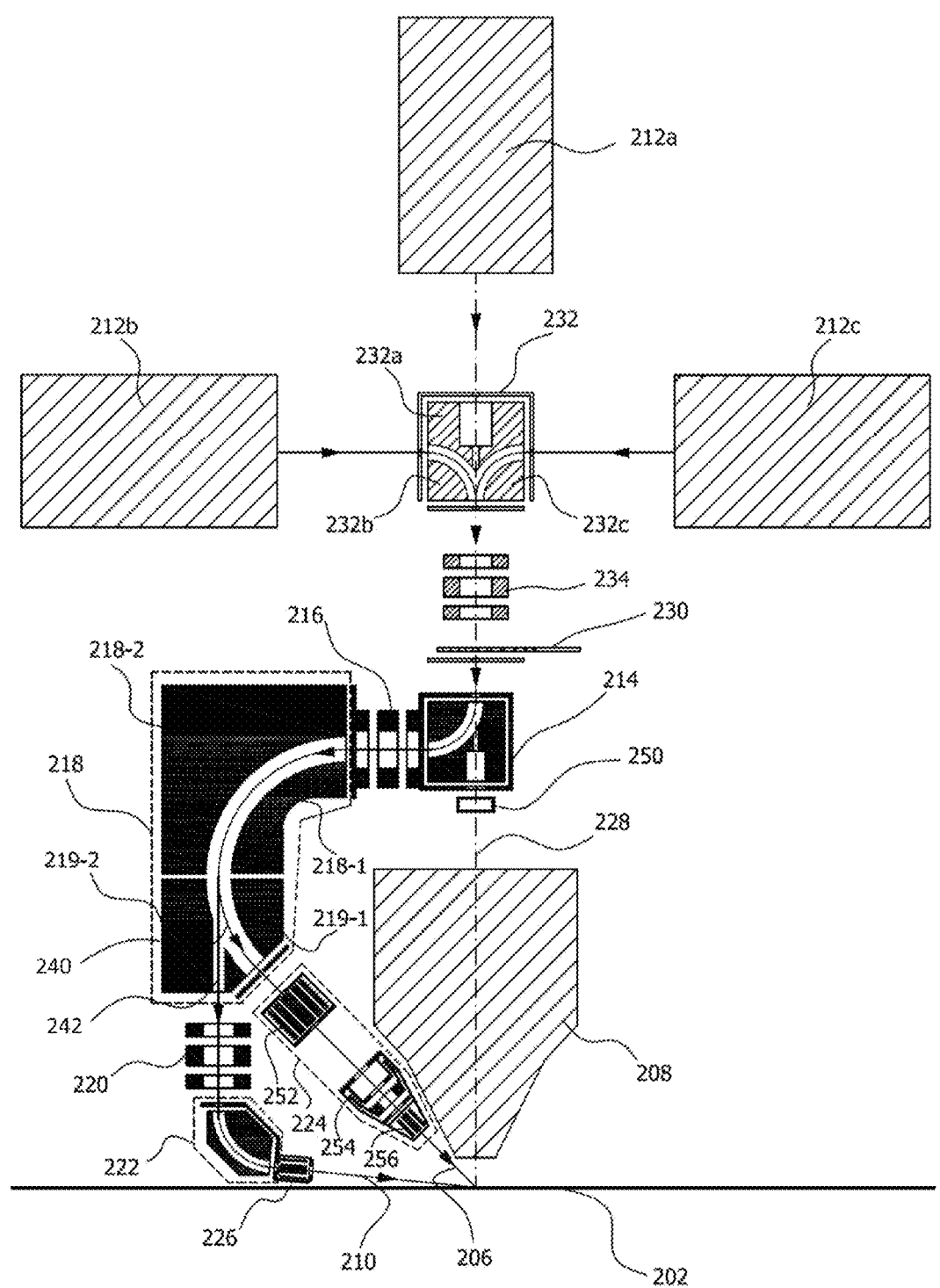
FIG. 3E shows exemplary rotatable ion beam optics for a unidirectional, double beam ion optical system with multiple top-mounted ion sources in accordance with the present invention.

For example, the bidirectional ion beam guide 218 in FIGS. 3A and 3C may be a bidirectional spherical deflector (see the rotatable ion beam optics of FIG. 3E). The bidirectional spherical deflector 218 may comprise a 135° spherical deflector (or condenser), sectioned by a narrow gap between two electrically isolated segments (90° deflector 218-1/218-2, and 45° deflector 219-1/219-2). The 90° deflector or segment includes internal spherical sector 218-1 and external spherical sector 218-2, and the 45° deflector or segment includes internal spherical sector 219-1 and external spherical sector 219-2. Sector 219-2 has an outlet channel that leads the ion beam 210 to the second ion beam path 242 in an orthogonal direction. The beam direction can be changed by switching the voltage of the electrodes 219-1 and 219-2. For the beam exiting to the first ion beam path 240 (e.g., in the 135° or FIB direction), the electrode 219-1 is electrically connected (e.g., shorted) to electrode 218-1, and electrode 219-2 is electrically connected (e.g., shorted) to electrode 218-2. For the beam exiting to the second ion beam path 242 (e.g., the orthogonal or GIB direction), electrodes 219-1 and 219-2 are electrically disconnected from electrodes 218-1 and 218-2, and connected to ground (V=0).

The apparatus 200 of FIG. 3A can therefore provide a wide range of the milling rate (e.g., from ~1 nm/min to ~20 µm/min). Aggressive milling can be performed using the ion beam 206 along the first ion beam path 240. The sample material removal rate during aggressive milling can be from 0.1-100 µm/min or any value or range of values therein (e.g., 0.3-20 µm/min). Gentle milling can be performed using the ion beam 210 from the second ion beam path 242. The sample material removal rate during gentle milling can be from 0.1-1000 nm/min or any value or range of values therein (e.g., 1-300 nm/min). In either case, the working distance of the ion beam optics from the surface of the sample 202 can be from 1-100 mm or any value or range of values therein (e.g., 10 mm during ion-milling).

The apparatus 200 of FIG. 3A includes a single ion source 212. In accordance with one embodiment of the present invention, the ion source 212 may comprise an ion optical subsystem configured to form the ion beam that is injected into the rotatable ion optical system. The ion source 212 may generate atomic, polyatomic or cluster ions having an energy in the range of 0.1-50 keV and a current in the range of 10 pA-100 µA for use in ion milling.

The optics in the apparatus 200 includes a changeable aperture 230 that provides a stepwise increase or decrease (attenuation) of the current of the ion beam injected into the rotatable ion optical system, the 90° spherical beam deflector 214, the first matching lens 216, and the bidirectional spherical deflector 218 that deflects the ion beam to either the first ion beam path (e.g., FIB module) 240 or the second ion beam path 242 onto the specimen 202 (e.g., a semiconductor wafer and/or integrated circuit). Referring to FIG. 3E, the FIB module 224 may include a beam stigmator 252, an objective lens 254, and a beam scanning plate 256. The second ion beam path 242 passes through a second matching lens 220, a grazing beam deflector 222, and a quadrupole beam compressor/aligner 226. The grazing beam deflector 222 deflects the beam at an angle of (90°−α), where a is the incident angle of the beam onto a surface of a planar specimen or sample 202 at 0°, as shown in FIG. 3A. The optics further includes an optional beam current monitor 250.

Examples of the ion beam shapes include round or circular beams, which may be particularly useful for polishing applications, and elliptical beams, which may be particularly useful for cutting applications. The diameter of the beams 206 and 210 output from the first ion beam path 240 and the second ion beam path 242, respectively, may be from about 2 µm to about 10 mm, or any value or range of values therein (e.g., from about 10 µm to about 2 mm), although the minimum diameter of the ion beam may depend on the ion source or type of ion source (e.g., a 20-30 nm beam diameter is achievable using a liquid metal ion source). The axial ratio of an elliptical beam 206 or 210 output from the first or second ion beam path 240 or 242 can be up to about 1:20 (e.g., up to about 1:10).

The rotatable optics in the system 200 thus provides dedicated multiple beams 206 and 210 (e.g., from either first path 240 or second path 242), from substantially any direction. A beam 210 may be directed at a first angle of >0° to about 20° along second path 242, or a beam 206 may be directed at a second angle of from about 30° to about 60° along first path 240. For example, the first and second angles may be about 6° and about 45°, as shown in FIGS. 3A and 3E, or any other value or range of values within the ranges given herein. As will be discussed below, the present apparatus enables steering of the beam(s) as well, with variable ion beam angles.

FIG. 3B is a diagram showing a bidirectional double-beam apparatus 200' that includes the common components described above, plus the ion source 212, a two-way ion beam deflector 214', first and second ion optical matching members 216a-b, first and second bidirectional ion beam guides 218a-b, first and second FIB modules or members 224a-b, first and second ion optical matching members 220a-b, and first and second ion beam deflectors 222a-b. The ion source 212 may be as described with regard to the system 200 in FIG. 3A, and the first and second ion optical matching members 216a-b, first and second bidirectional ion beam guides 218a-b, first and second FIB modules or members 224a-b, first and second ion optical matching members 220a-b, and first and second ion beam deflectors 222a-b may be as described with regard to the ion beam deflector 214, ion optical matching member 216, FIB modules or members 224, and ion optical matching member 220 ion beam deflector 222, respectively, in FIG. 3A.

The ion beam from ion source 212 may be switched between two separate and/or independent paths by the ion deflector 214'. The alternating beam is directed towards either the first bidirectional ion beam guide 218a or the second bidirectional ion beam guide 218b. The direction of the ion beam can be switched between the first and second bidirectional ion beam guides 218a-b at substantially any desired rate (e.g., on the order of seconds or minutes, down to milliseconds, microseconds or nanoseconds). The bidirectional double-beam apparatus 200' allows for substantially uniform milling or machining of a location in the specimen 202 from each of two opposed directions (e.g., using ion beams 240a and 240b, or ion beams 242a and 242b).

FIG. 3C is a diagram showing a "topside" configuration 200" of rotatable ion optics with two ion beam trajectories 240 and 242 and multiple ion sources 212a-c in accordance with one or more embodiments of the present invention. The ion sources 212a, 212b and 212c in the rotatable ion optics of FIG. 3C can be nearly any known or existing ion source (e.g., a liquid metal ion source [LMIG] 212a, a noble gas plasma ion source 212b, a cluster or molecular ion source ion source 212c, etc.). The different ions from the different ion sources 212a, 212b and 212c can be introduced or directed into the rotatable ion optics with a multi-beam guide or deflector 232. Alternatively, the different ions from the different ion sources 212a, 212b and 212c can be introduced or directed into the rotatable ion optics with two two-way beam combiners in series. The multi-beam, unidirectional system 200'' further includes an ion optical matching member 234, which in various embodiments may be or comprise a matching lens or two or more beam correction electrodes.

The multi-beam guide (or deflector) 232 provides a beam switching function among the various ion sources 212a, 212b and 212c. There are a variety of different components and methods for multidirectional injection of ion beams into a single ion beam line, as shown in FIG. 3C. For example, electrostatic or magnetic fields can be applied by the multi-beam guide or deflector 232 to an ion beam from one of the ion sources 212a, 212b and 212c in a manner similar to the bidirectional ion beam guide 218 as described above. Typically, only one ion beam is emitted from the ion sources 212a, 212b and 212c at a given moment in time.

For example, the multi-beam guide or deflector 232 may be or comprise a three-directional (3-way) electrostatic deflector comprising two symmetrically joined 90° spherical sectors (see the rotatable ion beam optics of FIG. 3E). The multi-beam guide or deflector 232 has one common external electrode 232a in the upper half, and two internal spherical sectors 232b and 232c. Common electrode 232a in the upper half of the guide or deflector 232 has an inlet or channel for injecting an ion beam in a straight or linear direction. Beam switching may be realized by switching the voltages between the electrodes 232a-c. For example, to inject a straight beam (e.g., an ion beam from ion source 212a), all electrodes are held at ground ($V_a, V_b, V_c$=0V). To inject an ion beam from ion source 212b, the common electrode 232a is held at a predetermined potential $V_a$, electrode 232b is held at a predetermined potential $V_b$, and electrode 232c is electrically connected (e.g., shorted) to the common electrode 232a. To inject an ion beam from ion source 212c, the common electrode 232a remains at the same potential $V_a$, electrode 232b is electrically connected (e.g., shorted) to the common electrode 232a, and electrode 232c is at a predetermined potential $V_c$.

FIG. 3D is a diagram showing a bidirectional multi-beam apparatus 200''' that includes the common components described above, plus the ion sources 212a-c of FIG. 3C, the two-way ion beam deflector 214' of FIG. 3B, first and second ion optical matching members 216a-b, first and second bidirectional ion beam guides 218a-b, first and second FIB modules or members 224a-b, first and second ion optical matching members 220a-b, and first and second ion beam deflectors 222a-b as described for FIG. 3B.

Advantages of the combined high- and low-angle ion optics (e.g., first and second ion beam paths 240 and 242) include providing high-angle optics (e.g., using the fine FIB from first path 240) for machining the sample 202 (e.g., precise cross-sectioning, cutting, hole drilling, etc.) and low-angle beams (e.g., GIBs from the second path 242) and optics for surface machining applications (e.g., polishing, gentle milling, etc.) in a single device or apparatus.

Exemplary "Bottomside" Rotatable Ion Beam Systems

FIGS. 4A-4D schematically illustrate exemplary rotatable unidirectional and bidirectional ion optical systems 300-300''' with one or more bottom mounted ion sources in accordance with the present invention. Components common to the optical systems 300-300''' include precision sample stage 304, surface imaging or analytical inspection device 308, and ion beam defining aperture 330. The precision sample stage 304, surface imaging or analytical inspection device 308, and ion beam defining aperture 330 are the same or substantially the same as precision sample stage 204, surface imaging or analytical inspection device 208, and ion beam defining aperture 230 in FIGS. 3A-D. Non-rotatable components are designated with hatched lines. The ion beam optics of ion optical systems 300-300''' can rotate around a main axis 328.

Figure 4A:
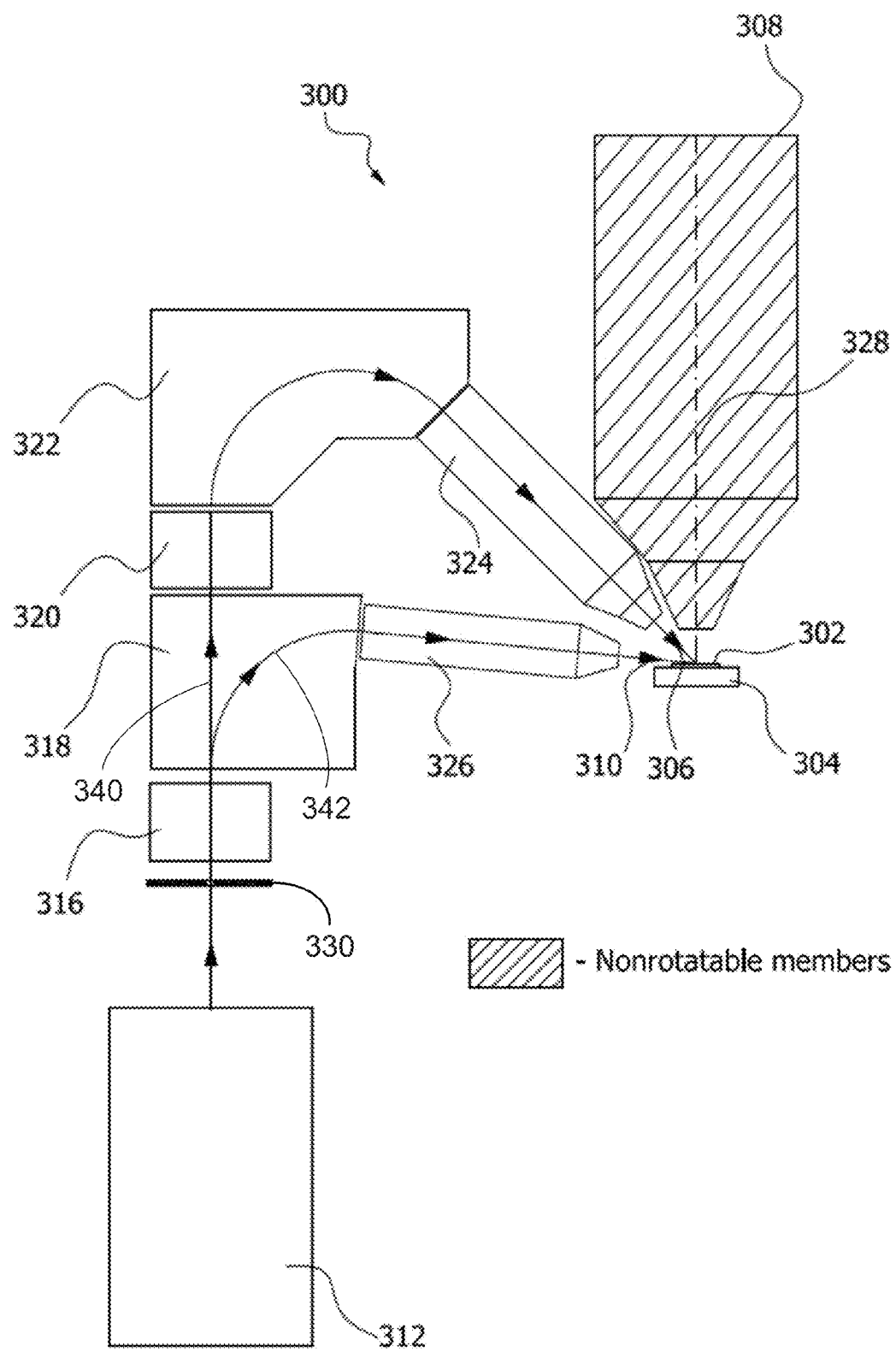

FIG. 4A shows a unidirectional, double beam apparatus 300 that provides high-angle (aggressive milling) ion optics using a first ion beam path 340 and low-angle (gentle milling) ion optics using a second ion beam path 342, similar to or the same as first and second ion beam paths 240 and 242 in FIG. 3A. The apparatus 300 further includes an ion source 312, an ion optical matching member 316, a bidirectional ion beam guide 318, a grazing ion beam (GIB) module or member 326, an ion optical matching member 320, an ion beam deflector 322, and a fine focused ion beam (FIB) module or member 324. The ion source 312 can be any kind of ion source suitable for ion milling, surface machining, or other use of an ion beam. The ion optical matching member 316 may comprise a matching lens or one or more beam correction electrodes. The ion optical matching member 320 may comprise a matching lens or beam correction electrodes. The fine focused ion beam (FIB) module or member 324 provides final focusing, shape correction, and scanning of the ion beam 306, as well as positioning of the beam 306 over the surface of the sample 302.

In the apparatus 300 of FIG. 4A, the bidirectional ion beam guide 318 redirects and/or switches the ion beam between the fast milling (path 340) and grazing milling (path 342) directions. As a result, the bidirectional ion beam guide 318 includes an inner electrode or internal spherical sector that directs the ion beam towards the grazing ion beam (GIB) module or member 326 upon application of an appropriate voltage. The angle at which the GIB 310 is redirected by the bidirectional ion beam guide 318 is >90°, but <120° (preferably ≤100°). In such a case, the bidirectional ion beam guide 318 and/or GIB module or member 326 provide(s) a final focus, beam shape, control and/or position of the grazing ion beam 310. The bidirectional ion beam guide 318 also includes an outer or external electrode or internal spherical sector that directs the ion beam towards the FIB module or member 324 upon application of an appropriate voltage.

The ion beam deflector 322 guides the ion beam 340 in the FIB direction. The angle at which the FIB 306 is guided by the ion beam deflector 322 is from 120° to 150° (preferably from 125° to 140°). In the apparatus 300 of FIG. 4A, the ion source 312 may be permanently connected to the ion beam optics, and may rotate with the ion beam optics (e.g., ion beam defining aperture 330, an ion optical matching member 316, bidirectional ion beam guide 318, FIB module or member 324, ion optical matching member 320, and ion beam deflector 322).

FIG. 4B shows a unidirectional, bottom-mounted double beam apparatus 300' in which the ion source 312 is located below the precision sample stage 304 and is aligned with the main rotational axis 328, but does not rotate with the ion beam optics. The apparatus 300' further includes an ion beam deflector 314 and a bidirectional ion beam guide 318'. The ion beam deflector 314 redirects the ion beam by 90°. The bidirectional ion beam guide 318' includes a lower section that redirects the ion beam by 90° and an upper section that includes internal and external spherical sectors or electrodes similar or identical to those in the bidirectional ion beam guide 318 of FIG. 4A. The stationary ion beam defining aperture 330 is arranged on or aligned with the main axis 328. The ion beam defining aperture 330 provides a coaxial entrance of the ion beam in the rotational stage of the apparatus or system 300'.

Figure 4C:
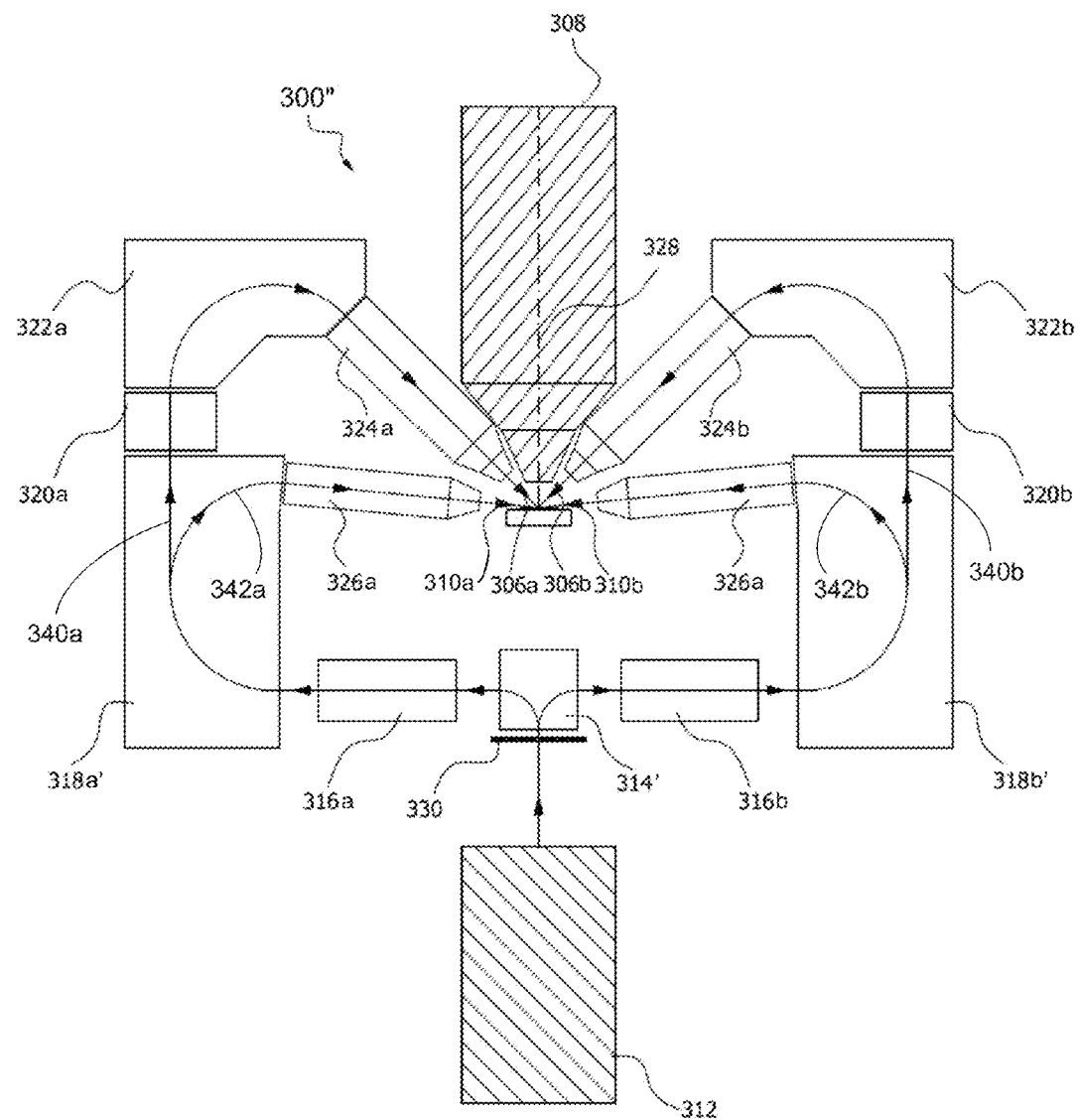

FIG. 4C shows a bidirectional, bottom-mounted double beam apparatus 300" in which the ion source 312 is located below the precision sample stage 304 and is aligned with the main rotational axis 328, but does not rotate with the ion beam optics. The apparatus 300" further includes an ion beam deflector 314' and a bidirectional ion beam guides 318a'-b'. The ion beam deflector 314' switches the paths of the ion beam from ion source 312 between two separate and/or independent (e.g., opposed) directions to form ion beams 340a-b or 342a-b, depending on the direction that ion beam guides 318a'-b' direct the ion beams. The bidirectional ion beam guides 318a' and 318b' are the same or substantially the same as the bidirectional ion beam guide 318' of FIG. 4B, and the ion beam defining aperture 330 is the same or substantially the same as in FIG. 4B. The ion source 312, ion optical matching members 316a-b, GIB modules or members 326a-b, ion optical matching members 320a-b, ion beam deflectors 322a-b, and FIB modules or members 324a-b are the same or substantially the same as in the apparatuses or systems 300-300' of FIGS. 4A and 4B.

Figure 4D:
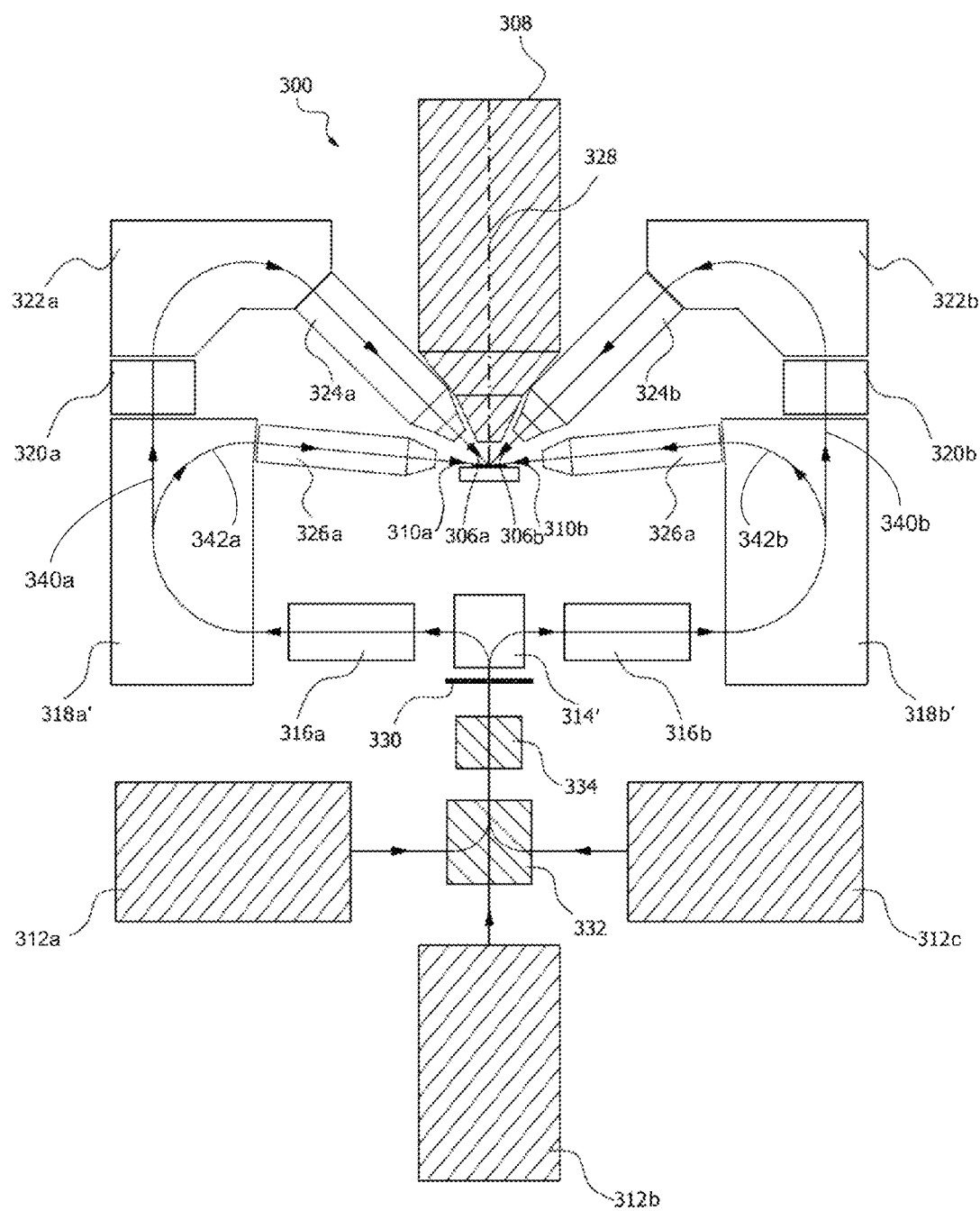

FIG. 4D shows a bidirectional, bottom-mounted double beam apparatus 300''' similar to the apparatus 300" in FIG. 4C, including multiple ion sources 312a-c located below the precision sample stage 304. The ion sources 312a, 312b and 312c are different from each other, and are independently a liquid metal ion source (LMIS), a plasma ion source, a noble gas ion source, an alkali metal ion source, a gas cluster ion source (GCIS), etc. The apparatus 300" further includes a multi-beam guide (or deflector) 332 with one or more beam switching functions and an ion optical matching member 334. The ion optical matching member 334 can comprise or be a matching lens or one or more beam correction electrodes. The ion beam defining aperture 330, multi-beam guide 332, and ion optical matching member 334 are aligned with the main rotational axis 328. The ion sources 312a, 312b and 312c, ion beam defining aperture 330, multi-beam guide 332, and ion optical matching member 334 do not rotate with the ion beam optics.

Exemplary Ion Beam Deflection Mechanisms for a Rotatable Ion Beam System

Figure 5B:
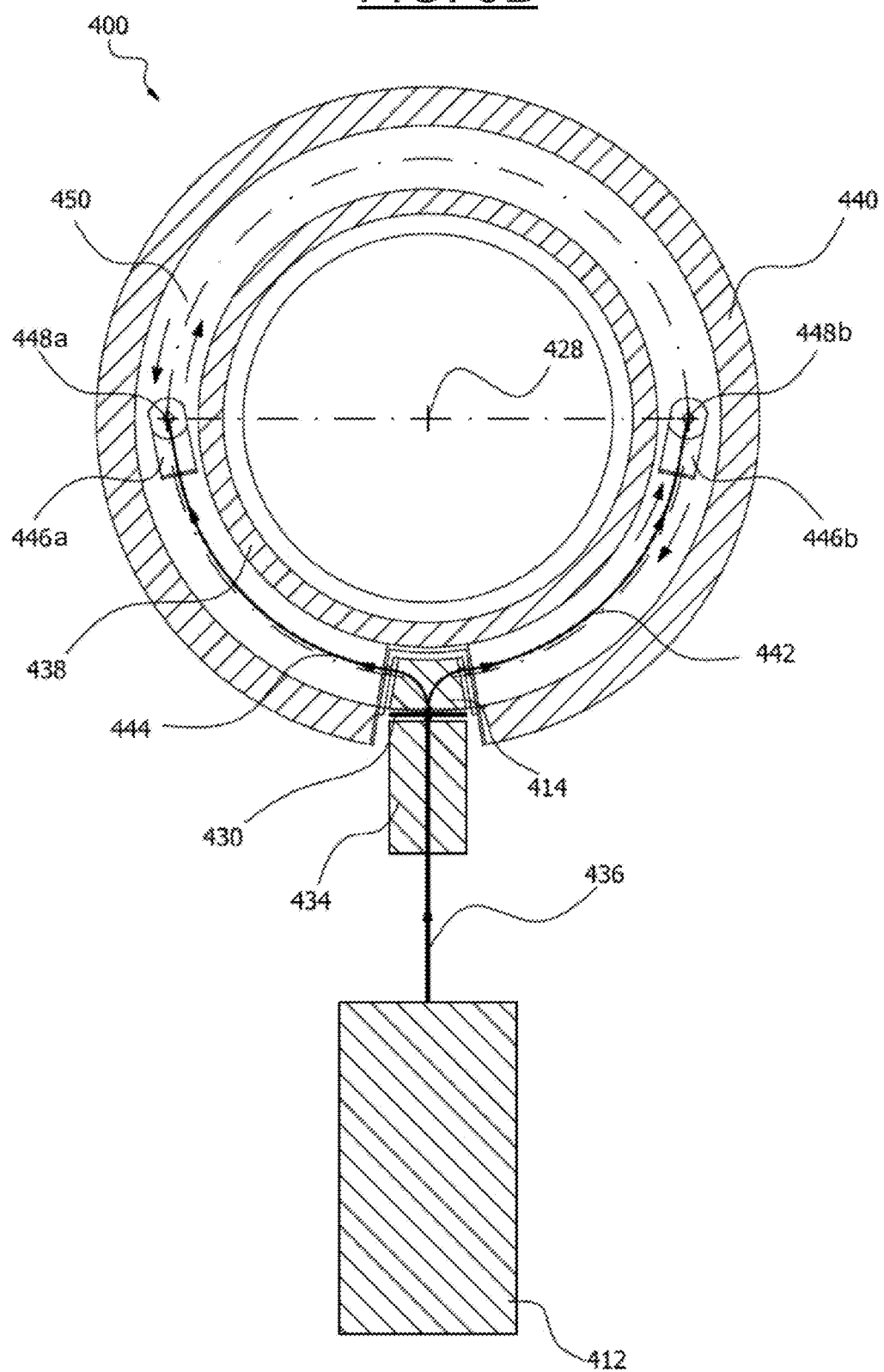

FIGS. 5A-5C schematically illustrate an exemplary rotatable, orbital, bidirectional ion optical system 400 comprising a spherical, circular, or toroidal electrostatic condenser in accordance with embodiments of the present invention. Ion source 412 (as described elsewhere herein) injects or emits an ion beam 436 to ion optical matching member 434, which may comprise one or more matching lenses and/or beam correction electrodes, and which may be substantially the same as ion optical matching member 334 (FIG. 4D) or 234 (FIG. 3D). The ion beam is then switched between two paths in opposed directions (e.g., clockwise beam rotation [see left ion beam 442] and counterclockwise beam rotation [see right ion beam 444]) by ion beam deflector 414. The rotatable, orbital ion optical system 400 may further include an ion beam defining aperture 430 (FIG. 5B). The ion beam defining aperture 430 provides a coaxial entrance for the ion beam 436 into the rotational stage of the system 400.

The electrostatic condenser guides the left and right ion beams 442 and 444 towards corresponding left ion beam deflector 448 and right ion beam deflector (not shown). The ion beam deflectors guide or lead the ion beams orthogonally out from the electrostatic condenser. A stationary surface imaging or analytical inspection device 408 (e.g., an optical metallographic microscope, laser microscope, electron microscope, mass spectrometer, or other surface analytical instrument) may be located inside the electrostatic condenser, which further includes an internal electrode 438, an external electrode 440, an upper plate 452, and a rotatable platform 450 for mounting and/or assembling the components of the rotatable ion optical system. The internal and external electrodes 438 and 440 may be spherical, cylindrical or toroidal. The internal and external electrodes 438 and 440, having predetermined voltages, provide orbital motion (e.g., rotation relative to the main axis 428; see FIGS. 5B-C) of the ion beam.

The ion source 412, ion optical matching member 434, and ion beam deflector 414 are stationary, and as a result, the external electrode 440, the internal electrode 438, and upper plate 452 are also stationary. Alternatively, the internal electrode 438 and upper plate 452 can rotate with the platform 450. The platform 450 and ion beam deflectors (e.g., 448) can rotate by up to nearly 180° (the ion beam deflector 414 act as rotational stop). Mechanical and electrical decoupling that allow the platform 450 to rotate while keeping the internal and external electrodes 438 and 440 stationary are known to those skilled in the art.

The ion beams exit from the condenser and enter ion optical matching member 416, which can be or comprise a matching lens or one or more beam correction electrodes, as discussed herein. The ion beams are then directed to either the FIB modules 424a-b or the GIB modules 426a-b by the corresponding bidirectional ion beam guide 418a-b. The ion beams directed to the GIB modules 426a-b also pass through an ion beam deflector 422 that guides the ion beam in the grazing direction. The rotatable optics may further include an ion optical matching member 420 (FIG. 5C) that may be or comprise a matching lens or one or more beam correction electrodes.

As described herein, the FIB modules or members 424a-b can provide final focusing, beam shaping and/or correction, and positioning of the ion beams 406 (FIG. 5C) over the surface of the sample, target, or specimen 402, and can also provide rastering or scanning of the ion beams (FIBs) 406 (e.g., for fast milling or cutting, etc.). GIB modules or members 426a-b can provide final focusing, beam shaping and/or control, and positioning of the grazing ion beams 410 for surface machining (e.g. polishing, gentle milling, grazing milling, etc.) of the sample, target, or specimen 402. The sample, target, or specimen 402 is held in place by sample stage 404, which can precisely position and hold sample, target, or specimen 402 according to X, Y, Z and tilt coordinates.

Figure 6A:
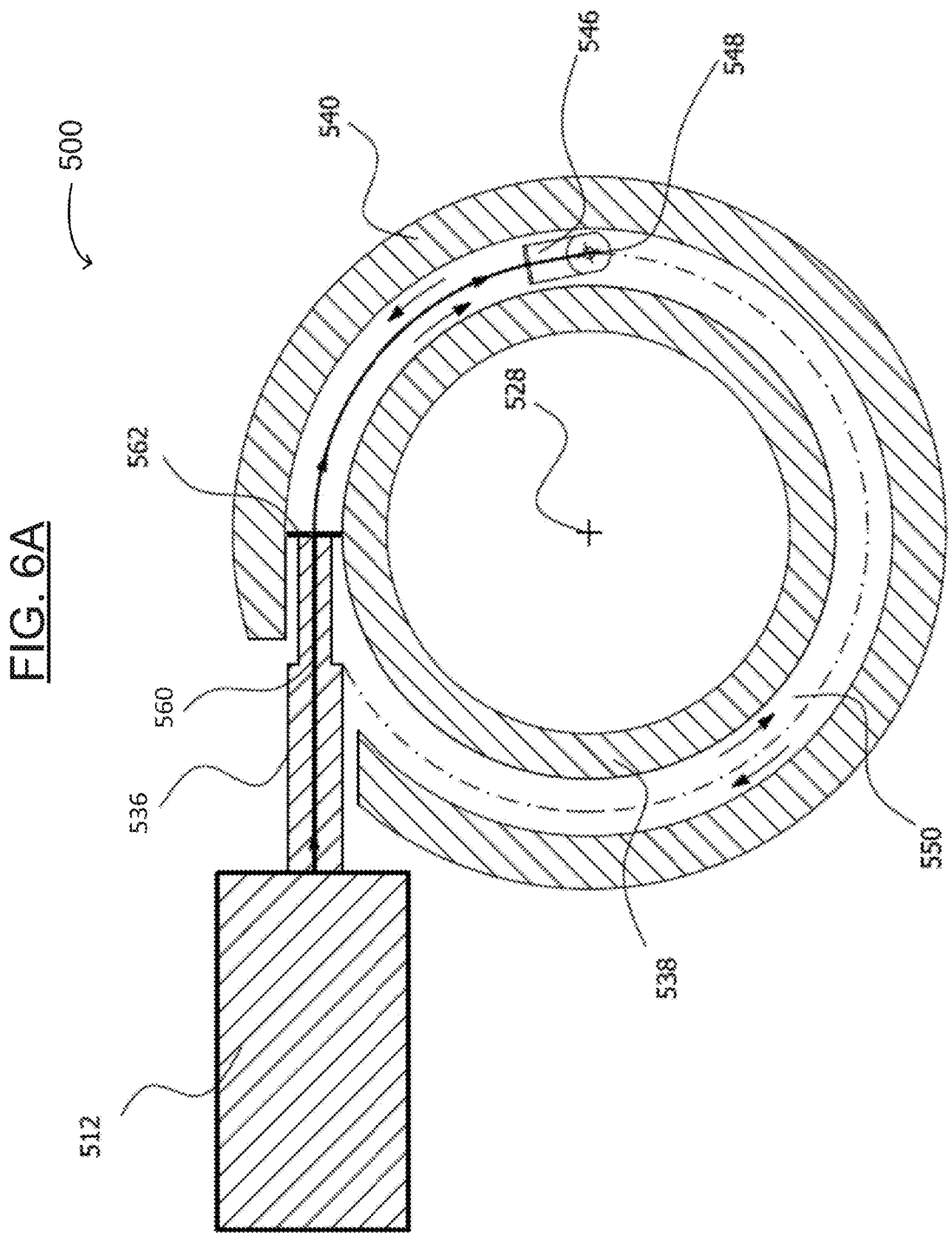

FIGS. 6A and 6B schematically illustrate alternative ion beam injection mechanisms for rotatable ion optical systems comprising a spherical, toroidal or circular electrostatic condenser in accordance with embodiments of the present invention. For example, FIG. 6A shows an orbital rotatable ion optical system 500 with a single ion beam injection mechanism. The system 500 includes an ion source 512 (as described herein), ion beam injection guide 536, an electrostatic condenser with spherical, cylindrical or toroidal internal and external electrodes 538 and 540, an ion beam deflector 546, and a rotatable platform 550 for mounting and/or assembling components of the rotatable ion optical system described herein. The internal and external electrodes 538 and 540, having predetermined voltages, provide orbital motion (e.g., rotation relative to the main axis 528) of the ion beam 560. The ion beam deflector 546 guides or leads the ion beam 560 orthogonally out from the electrostatic condenser at orthogonal exit point 548 in the rotatable platform 550. The orbital rotatable ion optical system 500 can rotate the ion beam optics up to nearly 360° (e.g., up to about 330° in one example) relative to a 0° reference point (e.g., the point or location where the ion beam exits aperture 562).

FIG. 6B shows an orbital rotatable ion optical system 500' with a double ion beam injection mechanism. The system 500' includes first and second ion sources 512a and 512b (as described herein, and which can be the same or different) that produce or emit left ion beam 542 and right ion beam 544. The system 500' operates substantially identically to the orbital rotatable ion optical system 500 of FIG. 6A, except that the ion beam optics can rotate up to nearly 180° (e.g., up to about 150° in one example) relative to a 0° reference point (e.g., the point or location where the ion beams exit apertures 562a and 562b).

Exemplary Rotatable Ion Beam Units

FIGS. 7A-D respectively show a layout, exterior/housing, and cross-sections of an exemplary interactive apparatus/system 200 in a topside configuration in accordance with one or more embodiments of the present invention. FIG. 7C is a cross-section of the apparatus/system 200 in FIG. 7A along the A-A line, and FIG. 7D is a cross-section of the apparatus/system 200 in FIG. 7A along the B-B line. The integrated beam unit (IBU) 200 includes an ion source 210, a multiple degree-of-freedom manipulator (not shown), rotatable optics 220, motor 225, a vacuum chamber 250, an interferometer 260, one or more endpoint detectors, and a number of optional components, including a laser 270. The motor 225 rotates the optics 220, for example by driving a wheel or disc 227 connected to the rotatable optics (e.g., at an uppermost location thereof). The endpoint detector(s) may include a visible or infrared light microscope 280, a thermo-vision device 282, or other device (such as an optical reflectometer) configured to determine whether one or more criteria satisfying an endpoint of the milling operation has been met. The integrated beam unit (IBU) 200 may further include a gas injection system (not shown) and a plasma source (not shown, but which may strike a plasma using one or more gases from the gas injection system).

The chamber 250 may be operably connected to a vacuum system capable of creating a relatively high vacuum (e.g., <$10^{-4}$ Torr, <$10^{-6}$ Torr, or any value <$10^{-4}$ Torr, such as <$5 \times 10^{-6}$ Torr). For example, the chamber 250 may be operably connected to a turbo-molecular and/or rotary pump, high and low vacuum gauges (for measuring the pressure inside the chamber 250), distributing valves, and a load-lock unit (see, e.g., FIG. 12A). A multiple gas supply system may provide one or more gases (e.g., Ar, Xe, or an Ar—Xe mixture) to the chamber 250 and/or to the ion source 210. The apparatus/system 200 may thus further comprise a gas injection system. The vacuum pump and/or system may be further equipped with a liquid nitrogen cold stage to trap potential contaminants and/or reactants for beam sensitive materials. The apparatus/system 200 may further comprise a maneuverable protective mask configured to protect areas of the specimen not to be milled and enable milling in the areas of the specimen not protected by the mask, and/or a depth profiler (e.g., comprising an interferometer) that measures the depth of a hole, cur or opening formed by the milling operation (e.g., for process quality control and/or end-point detection). The depth profiler may be fixed (e.g., comprising the interferometer and a suitable sensor) or scanning Milling process add-ons may include components for reactive gas-assisted ion etching (RIE) or plasma cleaning (not shown).

End-point detection of the milling process in the present apparatus or system may be monitored using an integrated optical imaging device. The optical imaging device may comprise a thermo-vision device 282. Alternatively, optical imaging device may comprise a visible light microscope 280. In any case, the chamber 250 may contain further optics 255 for reflecting, aligning and/or focusing light to or from the microscope 280, thermo-vision device 282, laser 270, and/or interferometer 260. In general, end-point detection in the present apparatus may comprise one or more of the following: (1) obtaining an image of interest from an imaging device; (2) measuring the milling depth using a microscope (e.g., by measuring a degree or amount of defocusing); and (3) measuring the milling depth by interferometry.

FIG. 8A is a diagram showing interior components 300 including an exemplary sample holder 310 and a table/manipulator 320 inside a system chamber in accordance with one or more embodiments of the present invention. As shown, the table/manipulator 320 has four degrees of freedom, for precise target alignment and positioning of the beam 342. Thus, the table/manipulator 320 may comprise an x-stage 322 configured to move the sample holder 310 left and right, a y-stage 324 configured to move the sample holder 310 forward and backward, a z-stage 326 configured to move the sample holder 310 up and down (vertically), and a tilt stage 328 configured to tilt or rotate the sample holder 310 angularly with respect to the x-y (e.g., horizontal) plane of the base 325, on which the various stages of the table/manipulator 320 are mounted. The x-stage 322 and the y-stage 324 and their associated functions are interchangeable (e.g., the x-stage 322 may move the sample holder 310 forward and backward, and the y-stage 324 may move the sample holder 310 left and right, or "322" may designate the y-stage, etc.).

The table/manipulator 320 further includes one or more motors and/or actuators (not shown) configured to move the x-, y-, z- and tilt stages 322, 324, 326 and 328 in the indicated directions. The motors and/or actuators for each of the stages may comprise piezoelectric motors, and the mechanism(s) by which the x-, y-, z- and tilt stages 322, 324, 326 and 328 move may include, e.g., a rack and pinion-type linear actuator, a hydraulic piston or cylinder, etc. The positional accuracy of the x-, y-, and z-stages in the table/manipulator 320 may be within ±1 μm (e.g., ±0.5 μm, ±0.2 μm, or any other value within ±1 μm).

The tilt stage 328 may rotate the sample holder 310 by an angle up to 90°−β, where β is the angle at which the ion beam 322 emerges from the second ion beam path 345 relative to a planar surface of the base 325 or the sample holder 310 or z-stage 326 when the tilt stage 328 is at an angle of 0°. In some embodiments, tilt stage 328 may rotate the sample holder 310 by a maximum angle in the range of from 45° to about 85° (e.g., 50°, 60°, or any other angle in such a range). The motor for the tilt stage 328 may move at a maximum angular speed of from 10° to 45° per second (e.g., 20° per second, or any other value in such a range).

The sample holder 310 is part of or affixed to the z-stage (vertical stage) 326 of the table/manipulator 320, but it can instead be part of or affixed to a different stage (e.g., the x-stage 322 or y-stage 324), Also, the various stages are not necessarily in the sequence shown, and the z-stage 326 may be positioned under the x- and y-stages 322 and 324, configured to raise the x- and y-stages 322 and 324 up and down (assuming that the sample holder 310 in part of or affixed to at least one of the x- and y-stages 322 and 324). The sample holder 310 may hold a sample having a maximum size or maximum dimensions of 300 mm×300 mmx100 mm (e.g., 150 mmx150 mmx50 mm, 60 mmx60 mmx20 mm, or any other dimensions within such limits).

The sample holder 310 holds a sample 330 in place during treatment with the ion beam 342. Generally, the sample holder 310 remains stationary while treated area 335 of the sample 330 is irradiated with the ion beam 342.

Components 300 also include ion beam optics (represented by first and second ion beam paths 340 and 345). Because of the two paths 340 and 345 and the tilt stage 328 of the table/manipulator 320, the ion beam optics are maneuverable at high and low angles. As described elsewhere herein, the ion beam optics are also rotatable around an axis defined by the path of movement of the z-stage 326, the optical path of the imaging system 350, or other reference line(s) and/or plane(s) that are orthogonal to a planar surface of the sample holder 310, z-stage 328 or base 325 when the tilt stage 328 is at an angle of 0°.

FIG. 8B is a diagram showing an exemplary, substantially complete system/apparatus 750 with an exemplary alternative table/manipulator 760 in accordance with one or more embodiments of the present invention. The apparatus 750 of FIG. 8B includes the integrated beam unit (IBU) 600 of FIGS. 7A-D, the table/manipulator 760, and an exterior cabinet 770. The table/manipulator 760 manipulates a sample holder 780 mounted on an uppermost surface thereof. The table/manipulator 760 moves in each of three orthogonal linear directions (e.g., using X-, Y- and Z-motors and/or actuators), and can tilt around an axis defined by the X- and Y-linear directions. Alternatively, the X- and Y-motors and/or actuators can be replaced with a single motor and/or actuator that rotates the sample holder in the X-Y plane (i.e., around the Z-axis), but such an arrangement may limit the ability of the sample holder to move the target location in along the X- and Y-axes. The table/manipulator 760 is mounted on and/or positioned between upper and lower walls/surfaces of the exterior cabinet 770. In part, the table/manipulator 760 may be sealingly mounted or affixed to an underside of the uppermost wall or surface of the exterior cabinet 770 to enable a vacuum to be made or formed in the chamber 650.

The motor 625 rotates the ion optics 620 by driving the wheel or disc 627 with an axle and gear/wheel mechanism 629. Other components in the apparatus 750 having the same identification number as in another figure are the same or substantially the same as in the other figure(s).

Alternative Exemplary Systems/Apparatuses

Figure 9:
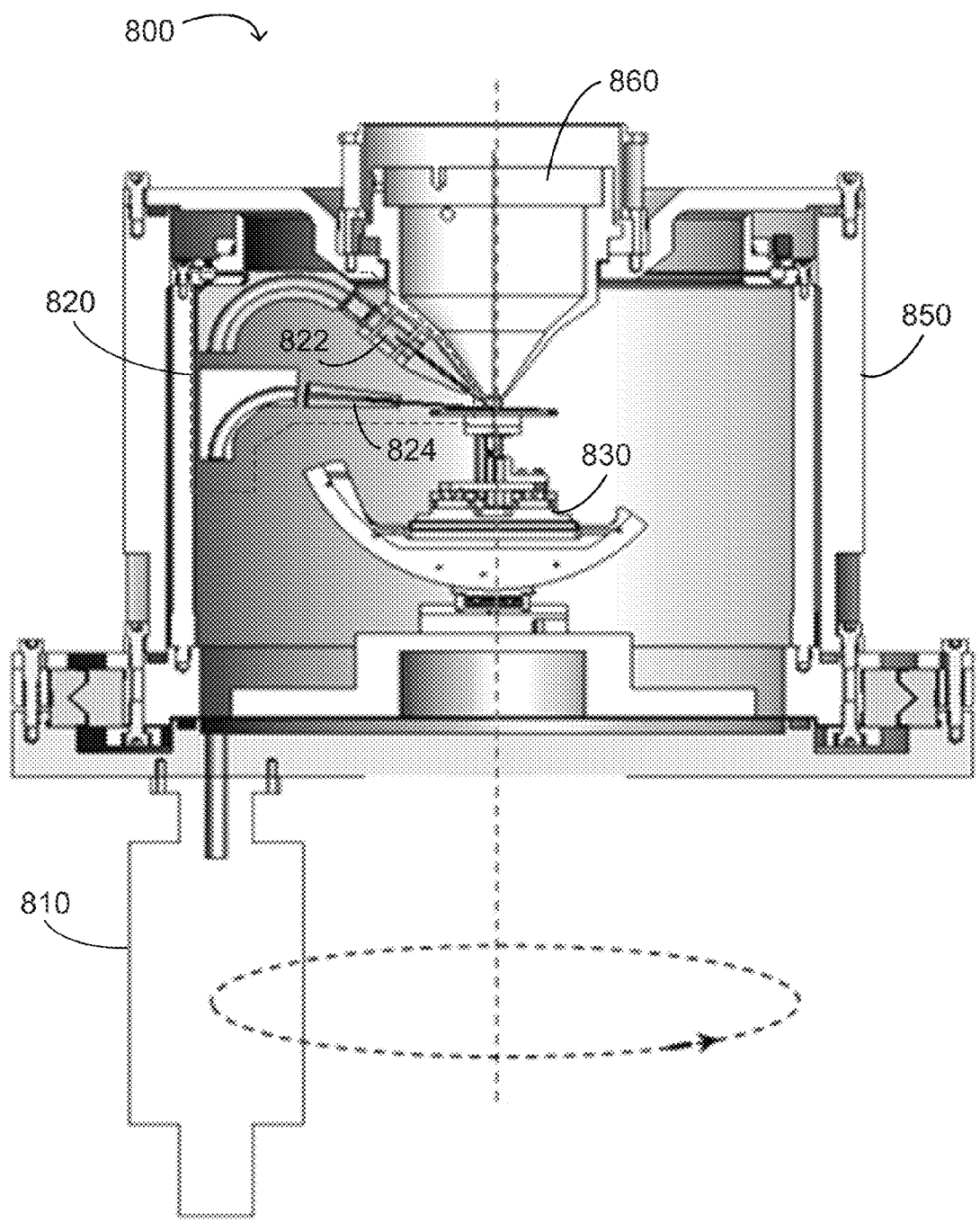
FIG. 9 is a diagram showing an exemplary downside configuration of the rotatable ion optics with two ion beam trajectories and one or more ion sources in accordance with one or more embodiments of the present invention.

FIG. 9 is a diagram showing an exemplary downside configuration of the rotatable ion optics with two ion beam trajectories and one or more ion sources in accordance with one or more embodiments of the present invention. The apparatus 800 includes ion source 810, ion optics 820, table/manipulator 830, chamber housing 850, and imaging device 860. The ion optics 820 includes first and second ion beam paths 822 and 824, similar to the first and second ion beam paths in other embodiments/figures. The optical imaging device 860 may comprise an integrated scanning laser or electron microscope (e.g., integrated SEM or LSM) or an optical metallographic microscope, any of which can be equipped with an imaging device such as a camera and used for endpoint detection.

In the configuration of the apparatus 800, the ion source 810 is below the table/manipulator 830, and the optical imaging device 860 is above the table/manipulator 830. The first and second ion beam paths 822 and 824 are above the table/manipulator 830, but the common components of the ion optics (not shown) are generally laterally adjacent to the table/manipulator 830. Such a configuration enables the optical imaging device 860 to be positioned directly above the area of interest on the sample 840. In one embodiment, the ion source 810 rotates with the ion optics 820.

Figure 10:
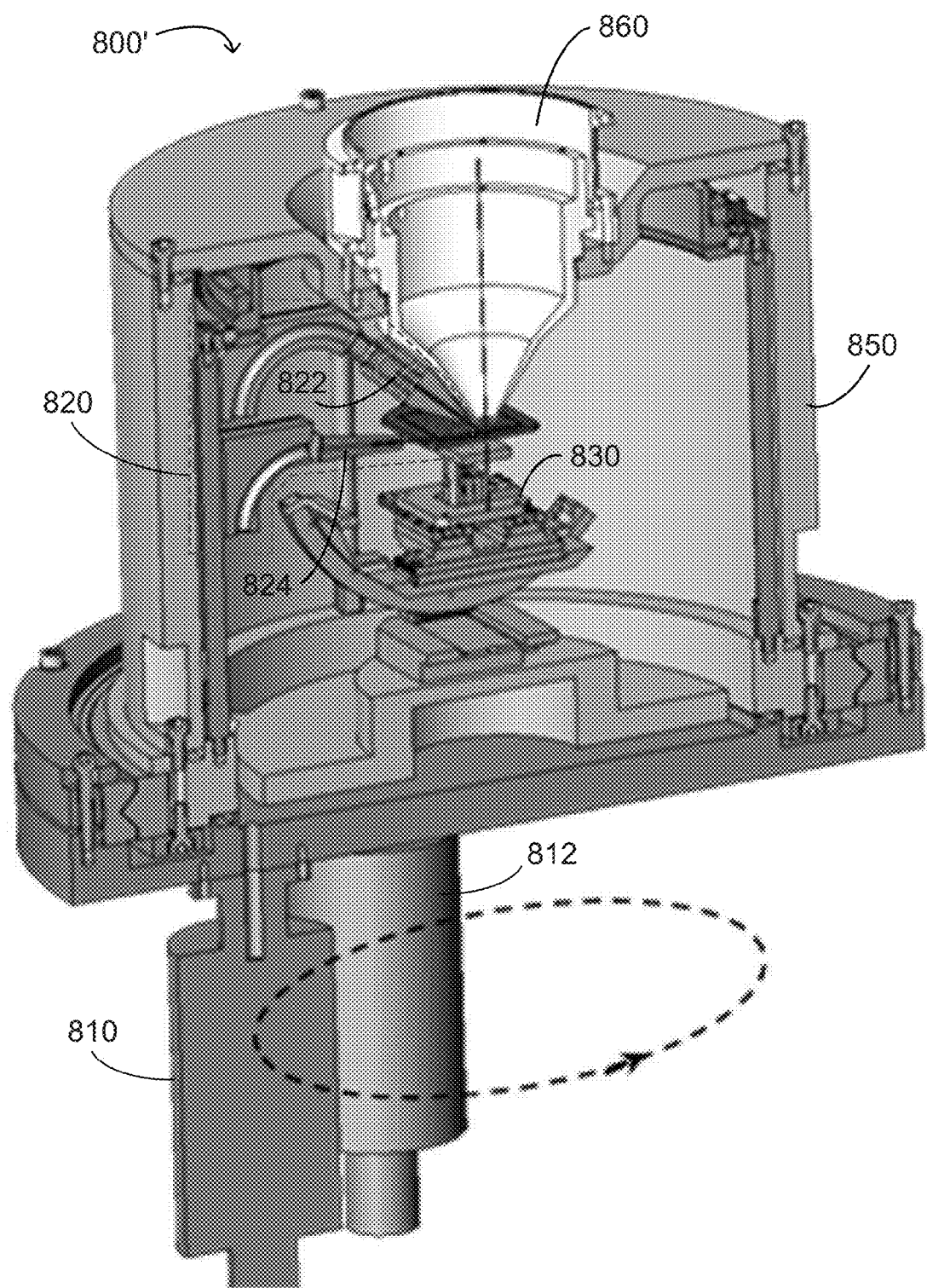
FIG. 10 is a diagram showing an alternative exemplary downside configuration of the rotatable ion optics with two ion beam trajectories and two interchangeable ion sources in accordance with one or more embodiments of the present invention.

FIG. 10 is a diagram showing an alternative exemplary apparatus 800' having a downside configuration of the rotatable ion optics 820 with two ion beam trajectories 822 and 824 and two interchangeable ion sources 810 and 812 in accordance with one or more embodiments of the present invention. The ion optics and ion sources in the apparatus of FIG. 10 can be as described herein for other apparatuses and/or systems, and are substantially as described for FIG. 9, except that the connection between the rotatable ion optics 820 and the ion sources 810 and 812 must be disconnectable and reconnectable so that the ion sources can be changed as needed and/or desired. As a result, the ion sources 810 and 812 can be independently rotated when disconnected from the ion optics 820.

Figure 11:
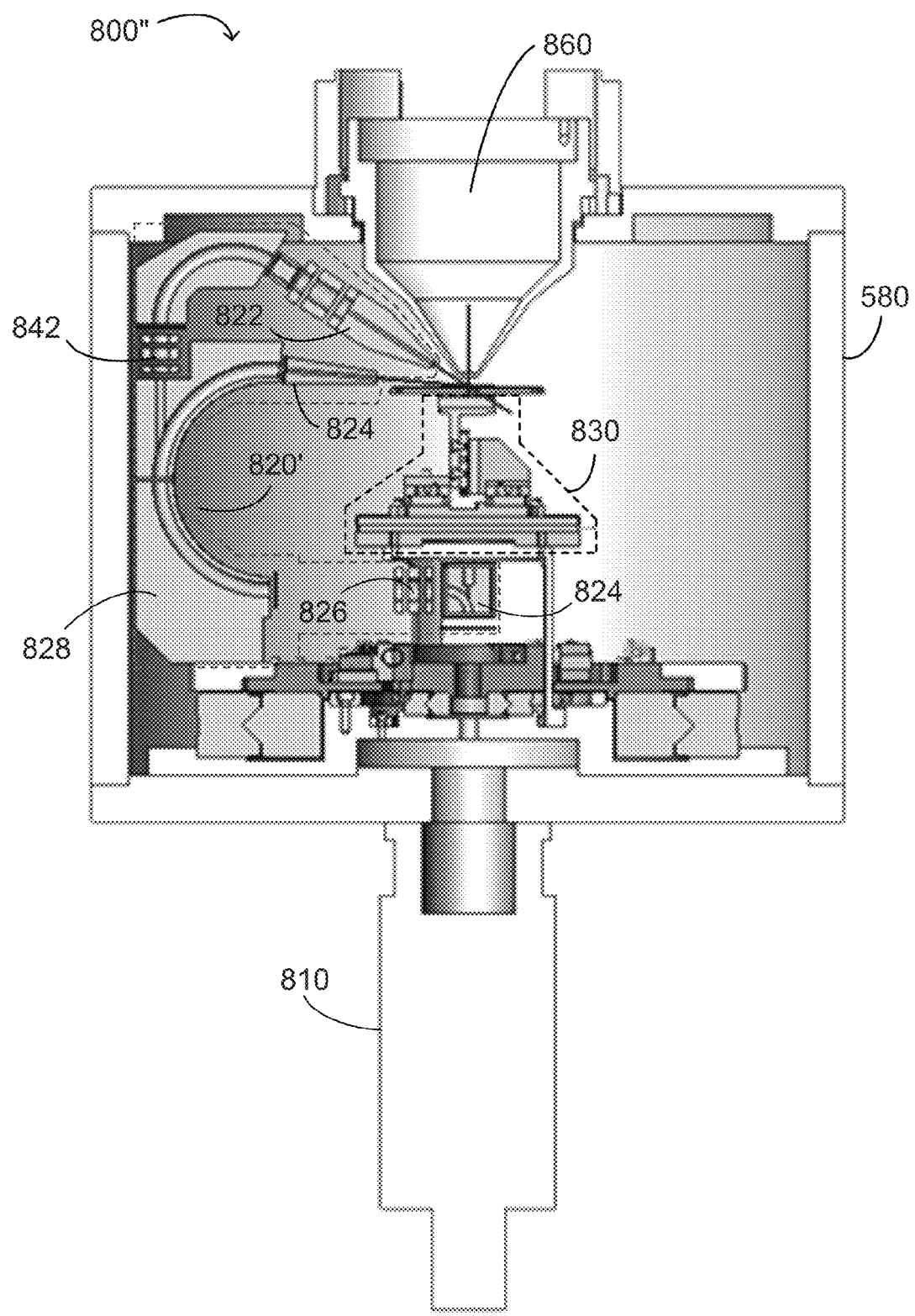
FIG. 11 is a diagram showing a further alternative exemplary downside configuration of the rotatable ion optics and a stationary ion source in accordance with one or more embodiments of the present invention.

FIG. 11 is a diagram showing a further alternative exemplary downside configuration of the rotatable ion optics 820' and a stationary ion source 810. The apparatus 800" includes ion source 810, ion optics 820, table/manipulator 830, chamber housing 850, and optical imaging device 860. The ion optics 820' includes first and second ion beam paths 822 and 824, similar to or the same as the first and second ion beam paths in other embodiments/figures. However, the ion source 810 is centered below the table/manipulator 830, and the ion optics 820' includes a 90° beam deflector 824 centered below the table/manipulator 830, and a first matching lens 826 between the 90° beam deflector 824 and a larger 90° beam deflector 828. The apparatus 800" may also include a beam current monitor (not shown) between the 90° beam deflector 824 and the table/manipulator 830. The second matching lens 842 may also be present in the embodiments of FIGS. 6-7.

Figure 12B:
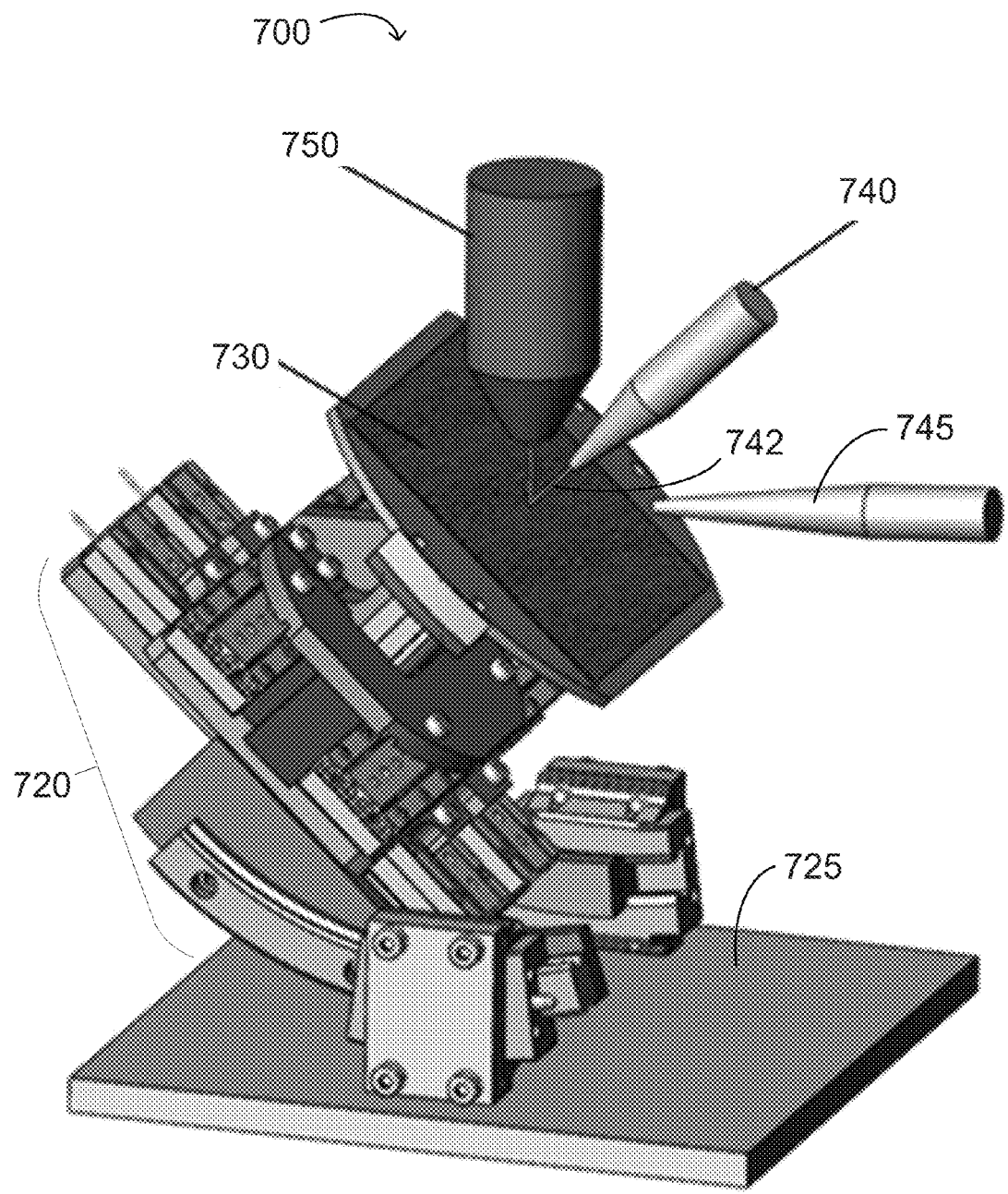
FIG. 12B shows the sample holder/table in the exemplary system and/or apparatus of FIGS. 8 and 12A in greater detail, in accordance with an embodiment of the present invention.

FIG. 12A is a diagram showing the exemplary system and/or apparatus 700 of FIG. 8A in a configuration for normal ion milling (i.e., where the sample is at a 90° angle to the ion beam emerging from first ion beam path 524). An air-lock 900, which is used for loading and unloading specimens to and from the vacuum chamber, is operably attached to a wall of the chamber. In addition to "traditional" ion milling, the system/apparatus can be used for other functions and/or processes (e.g., for making deep trenches or cuts, for anisotropic etching, for decorating grain boundaries, etc.). FIG. 12B shows the sample holder and table 700 from FIG. 8A in greater detail in the configuration for normal ion milling. Thus, in one example of an application on the present apparatus, the apparatus can be used for normal ion milling (e.g., to make deep trenches or cuts in the sample, to anisotropically etch the sample, to identify grain boundaries or decorate the sample, etc.). Normal ion-milling is generally conducted in a 90° configuration (i.e., where the ion beam 742 from the first ion beam path 740 irradiates the sample 730 at a 90° angle). The imaging system 750 can be used to monitor the endpoint of the normal milling operation.

Exemplary Applications

Technological methods and/or applications that can be performed by the present apparatus include:

1. Treatment of a statically positioned specimen by an ion beam with a chosen incident angle, energy, scanning range and dimension, and rotation around an area of interest, where the area of interest and an axis of the ion beam rotation are co-axial. This leads to controllable, planar removal of material in the area of interest to expose a target feature in the specimen.

2. Treatment of a statically positioned specimen by an ion beam with a chosen incident angle, energy, scanning range and dimension, and rotation around an area of interest with depth control using a laser interferometer. This allows real-time control of the removal of material from the sample to a pre-defined depth, as well as an ability to detect the end point of the process.
3. Treatment of a statically positioned specimen by an ion beam with a chosen incident angle, energy, scanning range and dimension, and rotation around an area of interest with simultaneous laser beam radiation of the area of interest at a chosen energy (or dose) and wavelength to activate atoms on the surface of the specimen. This allows an increased removal rate and controlled selectivity of the milling process. For example, a laser having an emission wavelength that is absorbed by a metal, but not by a surrounding dielectric, can be used to selectively heat the metal and thus remove the metal more selectively by ion milling.
4. Treatment of a statically positioned specimen by an ion beam with a chosen incident angle, energy, scanning range and dimension, and rotation around an area of interest that can be simultaneously observed by one or more imaging devices pre-aligned to the same focal point and co-axial with the axis of rotation of the ion optics. Preferable optical devices include high resolution optical microscopes and thermo-vision optical devices. For example, an optical microscope can be utilized to align the area of interest of a specimen with the axis of rotation of the ion optics to observe the area of interest during the milling process. A thermo-vision device can be utilized to (1) position the ion beam onto the specimen surface co-axially with the axis of rotation of the ion optics by recognizing the thermal trace of the ion beam, (2) position the laser beam onto the surface of the specimen co-axially with the axis of rotation of the ion optics by recognizing the thermal trace of the laser beam, and/or (3) control the specimen temperature in the area of interest.
5. Alternating treatment of the front side and backside of a statically positioned specimen (e.g., a semiconductor wafer) by an ion beam with a chosen incident angle, energy, scanning range and dimension, and rotation around an area of interest. The front side can be treated at a glancing angle, and the ion optics rotated around an area of interest to a preset depth or until a target feature is exposed. The transition between treatment of the front side and backside of the specimen is done by the sample (e.g., wafer) flipping. The backside treatment can be done by combining simultaneous laser beam radiation with ion-milling at a high incident angle (which is expected to increase the milling rate) and rotating the ion optics around the area of interest to the preset depth or until exposure of a target feature. This allows preparation of one or more plan view STEM samples within a single specimen or wafer without using repeated out-of-wafer sample extractions.

Thus, applications of the present apparatus and method include:
1. Real-time controlled ion-polishing
2. Site specific delayering for:
    2.1. SIMS, Auger analysis and depth profiling
    2.2. Electrical microprobing, Scanning Probe Microscopy
    2.3. 3D image reconstruction
3. SEM sample preparation:
    3.1. Cross-sectioning
    3.2. Plan view sample
    3.3. Post-FIB cleaning (e.g., cleaning after traditional FIB, in which the specimen often suffers induced damage from relatively heavy ions such as Ga)
    3.4. Grid-less electron transparent TEM sample preparation for SEM in STEM mode
    3.5. SEM sample cleaning (e.g., in situ)
4. TEM/STEM sample preparation:
    4.1. TEM cross-sectioning
    4.2. TEM plan viewing
    4.3. Post-FIB final thinning and cleaning for TEM
5. Sample extraction out of a bulk material or object (e.g., lift-out)
6. Micro hole drilling
7. Multicrystalline decoration The following examples show various applications of the present system(s) and method(s).

Figure 13A:
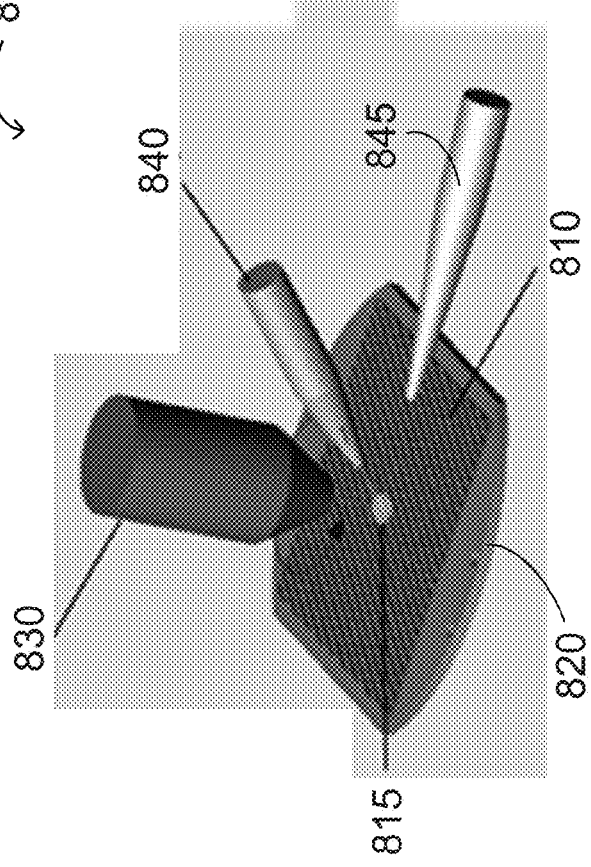
FIGS. 13A-B respectively show aggressive milling using high-angle ion optics and gentle milling using low-angle ion optics in a single apparatus in accordance with one or more embodiments of the present invention to delayer a large area of a sample.
Figure 13B:
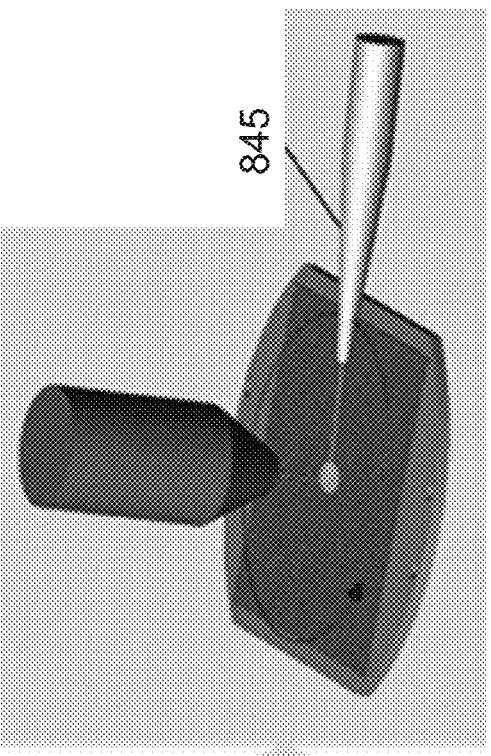

FIGS. 13A-B respectively show how a combination of aggressive ion milling using high-angle ion optics 840 and gentle ion milling using low-angle ion optics 845 in a single apparatus 800 in accordance with one or more embodiments of the present invention can delayer a large area 815 of a sample 810 (e.g., an integrated circuit) to a predefined depth. FIG. 13A shows aggressive milling at high angle using high angle ion-optics 840 on a stationary sample 810. FIG. 13B shows gentle milling at a low angle using low angle ion-optics 845 on the stationary sample 810. The treated area is designated 815. The process can be monitored using imaging system 830. As the optics rotate around the central axis of the system 800 (defined in FIGS. 13A-B as the light entering the imaging system 830), the material(s) and/or structure(s) in the treated area 815 is milled uniformly from all or substantially all directions. In one example, the present apparatus delayered and ion polished an area >10 μm×10 μm of the integrated circuit sample 810. The delayered and ion polished area was clean and in-focus.

Figure 14:
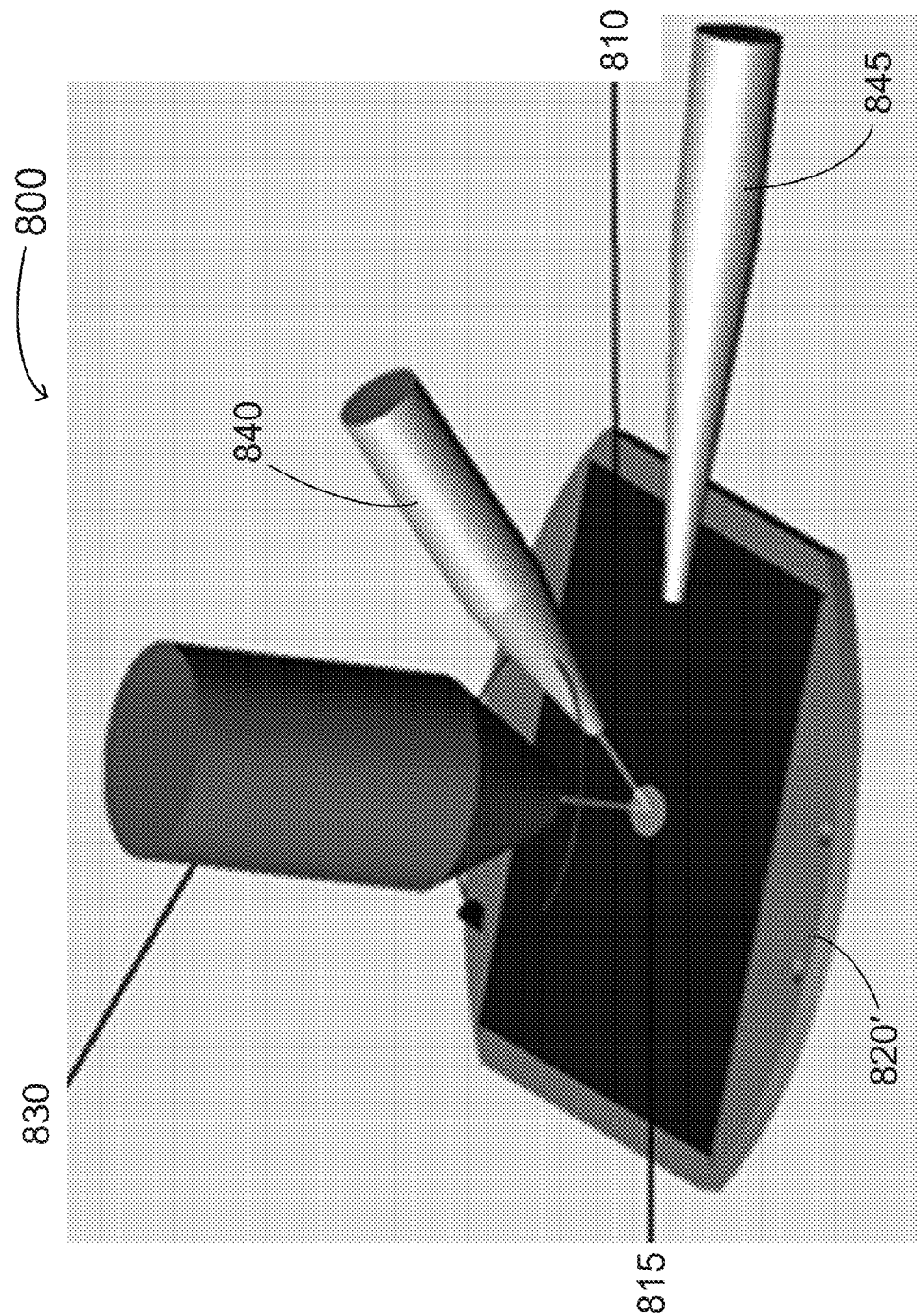
FIG. 14 is a diagram showing aggressive milling using high-angle ion optics to thin the back side of a wafer in accordance with one or more embodiments of the present invention.

FIG. 14 is a diagram showing aggressive milling using the high-angle ion optics 840 in the rotatable ion beam system 800 to thin the back side of a semiconductor/integrated circuit wafer 810 in accordance with one or more embodiments of the present invention. The purposes for such an application include elemental and molecular depth profiling at the nano-scale with analytical techniques (e.g. SIMS, Auger, XPS or Raman spectroscopy), and sample preparation for photoemission and LVx microscopy (e.g., at the chip level). The treatment area 815 may have a size (e.g., diameter) of from about 10 μm to several mm. The benefits of using the present rotatable ion optics 800 include superior planarity and roughness of a sputter crater (as compared to state of the art depth-profiling instruments) and minimal impact on the thermal and electrical integrity of the sample 810 (e.g., due to site-specific, non-contact milling). Simultaneous irradiation of the treatment area 815 with a laser having an emission wavelength that is absorbed by the substrate can heat the substrate and increase the milling rate.

FIGS. 15A-B respectively show front- and back-side milling of a sample 910 using a reversible sample holder 920 to prepare the sample 910 for transmission electron microscopy (TEM) using the low-angle ion optics 945 in a rotatable ion beam system 900 in accordance with one or more embodiments of the present invention. Milling in this example can be performed for preparation of a plan-view (or overhead view) TEM of the sample 900. FIG. 15A shows front-side milling of the sample 910 on a grid (not numbered) on the TEM sample holder 920 using the low-angle ion optics 945. An imaging system 930 can monitor progress of the process. Rotation of the optics around the central axis of the system 900 (defined by the light entering the imaging system 930) mills and/or polishes the material(s) and/or structure(s) in the treated area on the front side of the sample 910 uniformly from all or substantially all directions. FIG. 15B shows back-side milling of the sample 910 using the low-angle ion optics 945 after turning or flipping the sample holder 920 by 180°. Rotation of the optics rotate around the central axis of the system 900 mills and/or polishes the material(s) and/or structure(s) on the back side of the sample 910 (in the same area treated on the front side of the same 910) uniformly from all or substantially all directions. In the example shown in FIGS. 15A-B, the TEM sample holder 920 may be reversible (or "flippable"), enabling ion beam treatment of both the front side and the back side of the sample 910 in the same location. In one example, a STEM image of a large area (>10×10 μm) of a sample integrated circuit manufactured using an advanced technology node (e.g., sub-45 nm or sub-32 nm) was prepared.

FIGS. 16A-B respectively show grid-less SEM sample preparations for STEM imaging by sequential front and back side milling of a sample 810 to TEM thickness using the exemplary rotatable ion beam optic system 800 in accordance with one or more embodiments of the present invention. No preprocessing is required, as is generally required in sample extraction out of a bulk sample, or placement of a prethinned sample on a standard TEM grid. FIG. 16A shows front-side milling of a treated area 815 in a grid-less sample 810 using both high angle (e.g., FIB) optics 840 and low angle (e.g., GIB) optics 845. Generally, the high angle optics 840 and low angle optics 845 are operated sequentially, rather than simultaneously, but some embodiments may mill the sample 810 simultaneously with both high angle optics 840 and low angle optics 845. The process may be monitored using the imaging system 830. FIG. 16B shows back-side milling to STEM thickness after flipping or rotating the sample holder 820' by 180° to form a grid-less STEM lamella 815'. Rotation of the optics around the central axis of the system 800 (defined by the light entering the imaging system 830) during both front-side and back-side milling mills and/or polishes the material(s) and/or structure(s) in the treated area 815/815' uniformly from all or substantially all directions.

FIG. 16C shows a wafer or segment thereof with multiple site-specific grid-less electron transparent lamellas 815*a-c* in accordance with one or more embodiments of the present invention. Thus, the present system(s) and method(s) can prepare unique site-specific grid-less STEM samples. Limitations on sample size and observation area (e.g., in a STEM mode) associated with lift-out techniques are not present in the present system(s) and method(s). For example, combined front- and back-side thinning of a SEM sample to TEM thickness can be performed over a relatively large area (e.g., >200 μm$^2$) using the present system(s) and method(s). Final TEM lamellae thicknesses below 10 nm have been achieved. Thus, front and back side milling of a SEM sample to TEM thickness can be performed using the present apparatus and method(s) for analysis in STEM mode (no TEM grid is required).

Figure 17A:
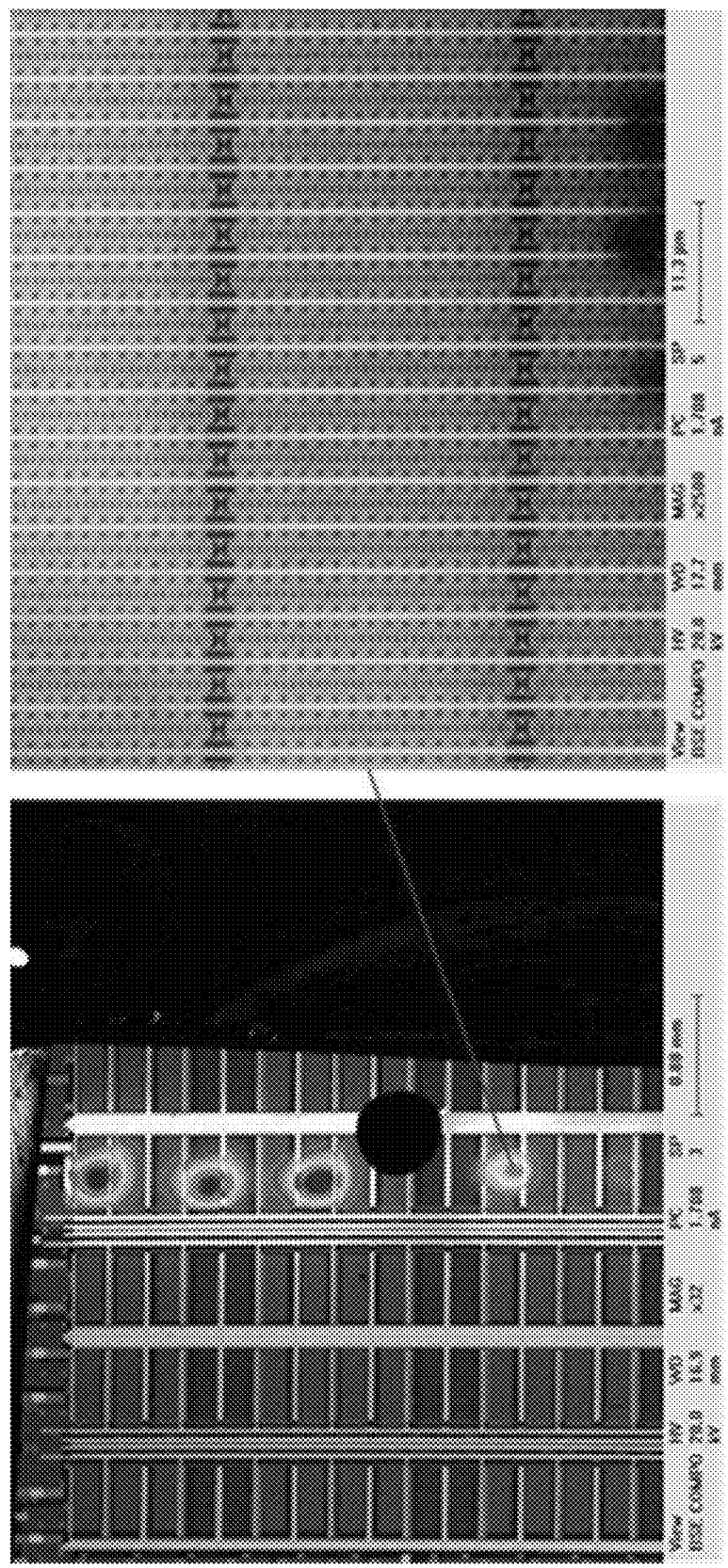
FIGS. 17A-B are photographs of a sample subject to multi-site delayering.

FIG. 17A is a photograph of a sample subject to multi-site delayering. The sample shown is a memory block in a semiconductor integrated circuit. The right-hand image is of the lowermost delayered spot in the left-hand image, magnified 2500×. The delayering spots in the left-hand image (magnified 32×) vary from 50 to 200 microns in width. However, the target areas that can be delayered using the present apparatus and method may be from 0.01 to 10 mm across, or any value or range of values therein (e.g., 0.5 to 3 mm). The present apparatus and method can also be used to target particular areas or regions of a sample. The target areas or regions may be pre-aligned for delayering using cross-hairs on a monitor or other display, for example.

Figure 17B:
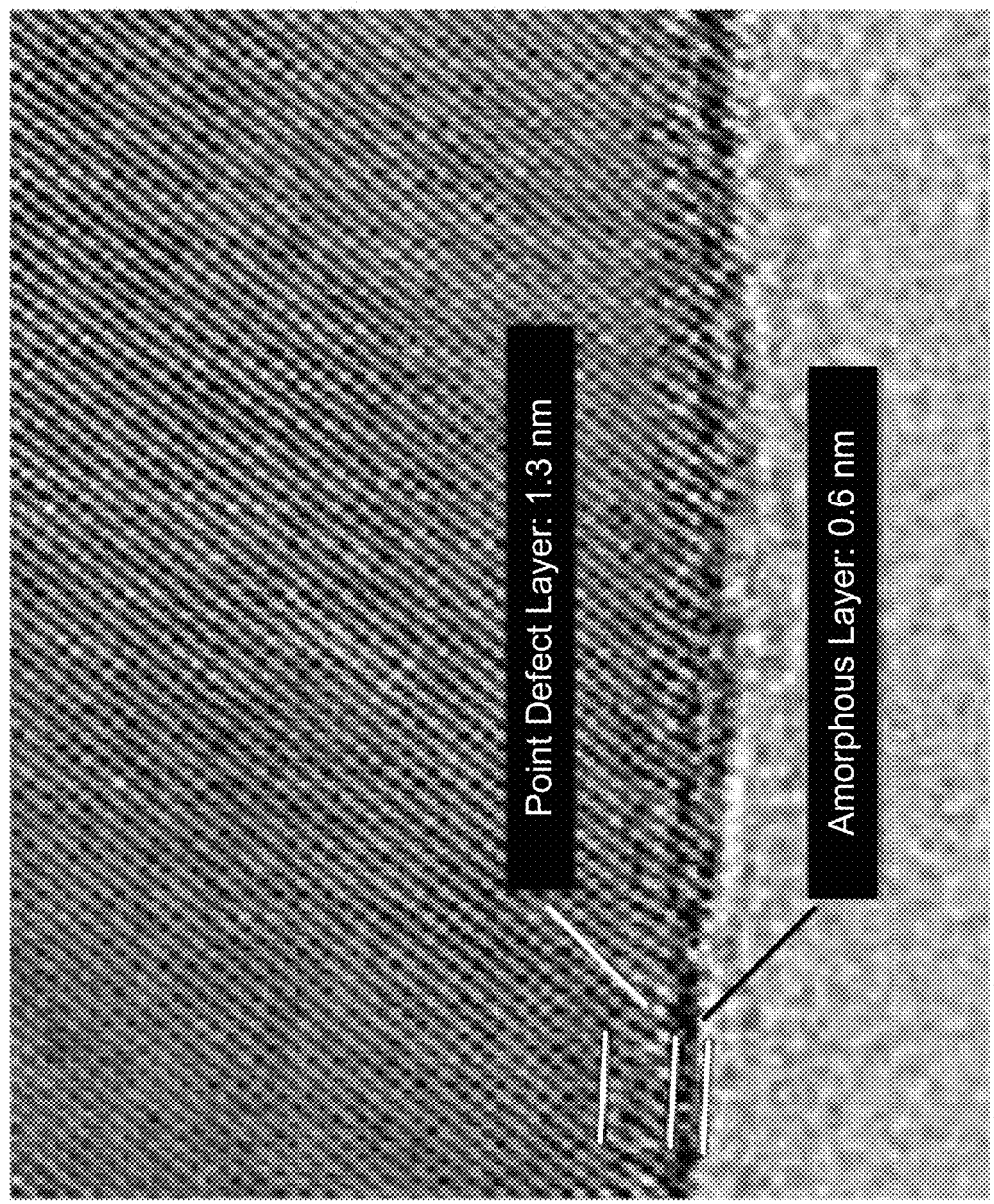

In another example, post-FIB final thinning of TEM samples and post-FIB cleaning of damage and defects induced by ion bombardment (e.g., cleaning FIB-induced damage) were studied. The FIB target was aligned and the beam positioned on the target. The selected target was milled at both high and low angles. The process was monitored using an imaging system aligned with a central axis of the rotatable optic system. The TEM sample (FIG. 17B) was prepared as follows: 1) Ion irradiation was performed (e.g., FIB with rotation, followed by GIB with rotation) to induce a damaged layer and surface amorphization in the sample. 2) A TEM cross-section of the irradiated area was taken. Parameters of the ion bombardment included an ion beam energy of 1 KeV and ion beam incident angle of 7° (i.e., low-angle milling) for a duration of 3 min. A cross-section of the TEM sample by FIB (i.e., high-angle milling) @1.6 kV showed about 0.6 nm of amorphization (i.e., an amorphous layer of about 0.6 nm thickness), and a layer of about 1.3 nm thickness containing point defects. Thus, the present invention enables negligible surface amorphization, minimal depth of the damaged layer, and/or superior lattice image quality of TEM samples.

Figure 18:
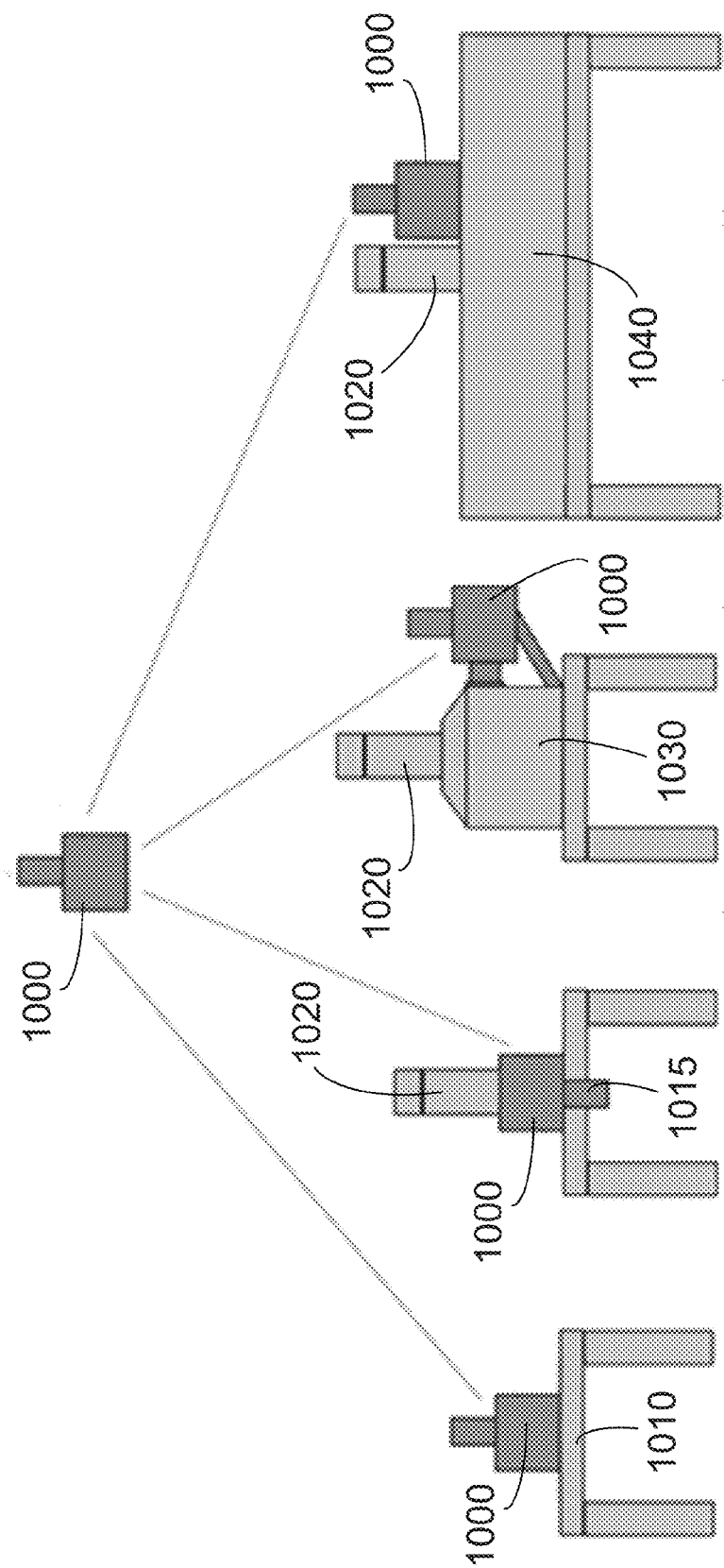
FIG. 18 is a diagram of various exemplary combinations of the present apparatus with other tools in accordance with embodiments of the present invention.

FIG. 18 is a diagram of various exemplary combinations of the present apparatus with other tools in accordance with embodiments of the present invention. For example, a stand-alone optical based system 1000 can be installed on a small, vibration-resistant (or damped) table 1010. A stand-alone SEM-based system may include the present system 1000 with rotatable ion beam optics and a scanning electron microscope 1020, in which the ion source 1015 is in a "bottomside" configuration. The present ion beam system 1000 can be integrated with an SEM 1020 and another analytical tool 1030, or with a wafer inspection system 1040. Other combinations and applications are envisioned, and are encompassed by the present disclosure.

Exemplary Methods of Sample Preparation and/or Processing Using Ion Milling

Figure 19:
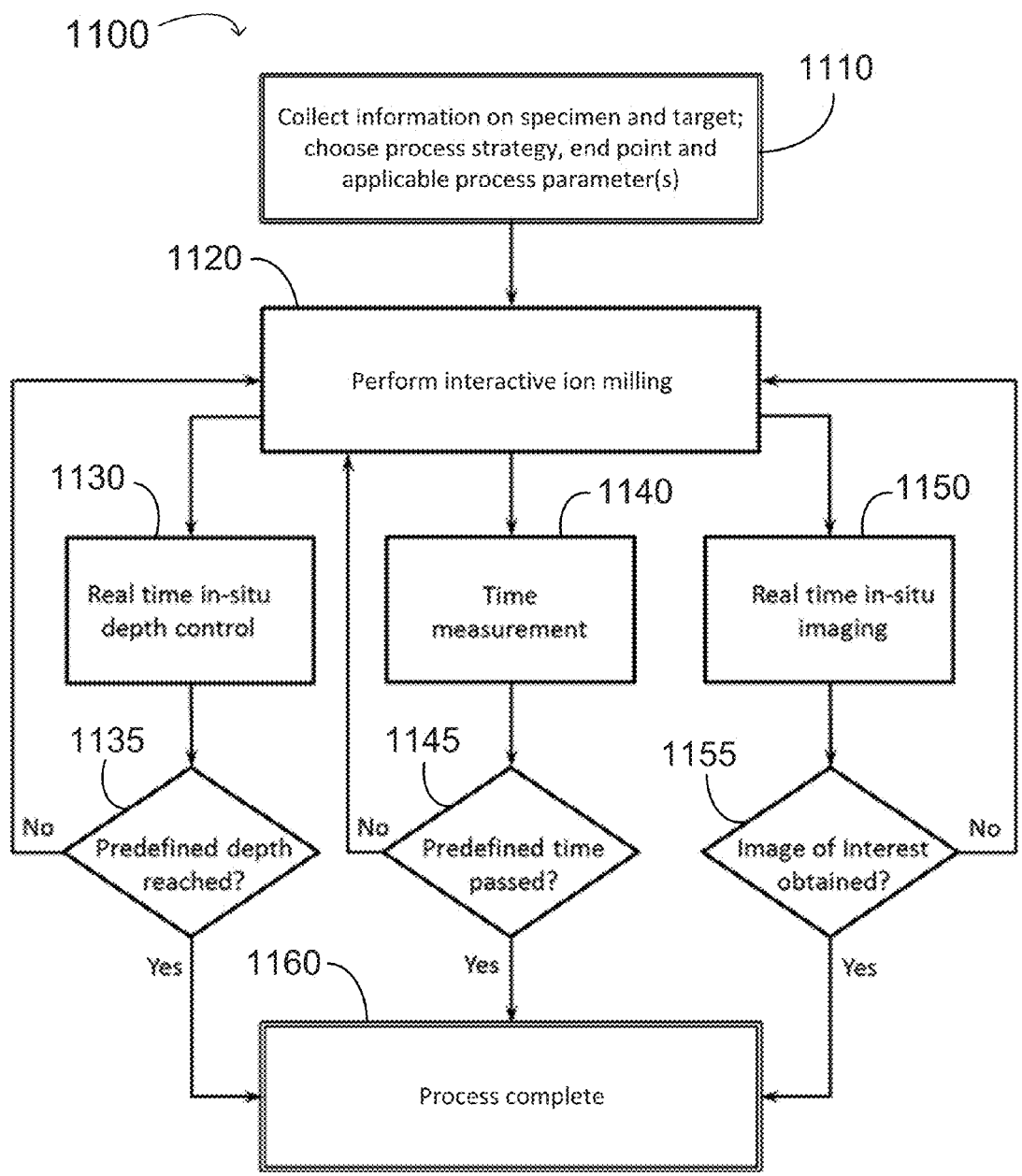
FIG. 19 is a flow chart showing exemplary methods of sample preparation and/or imaging in accordance with one or more embodiments of the present invention.

FIG. 19 is a flow chart 1100 showing exemplary methods of sample preparation and/or processing in accordance with one or more embodiments of the present invention. The methods reflect an approach to real-time control of micromachining and applications thereof to sample analysis, failure analysis, etc., using a variety of techniques with a single apparatus.

At 1110, information is collected on the specimen and the target or region of interest. In general, this is also when the end-target is anticipated. A process strategy is chosen, a target or desired end point is selected or determined, and any applicable processing parameter(s) is/are selected or determined.

At 1120, interactive ion milling is performed. In general, as ion milling is performed, the process is monitored. Ion milling may comprise milling or cutting the specimen with a focused ion beam (FIB), or milling or polishing the specimen with a grazing ion beam (GIB). The milling process may be monitored by real-time visualization (e.g., optical microscopy [alone or with imaging at 1150], thermal imaging, etc.). Monitoring may also be conducted by measuring the time of the milling process (and knowing the milling rate under the processing conditions, which can be determined empirically) at 1140, or by measuring or controlling the depth of the milling process (e.g., by measuring the depth using an imaging process, or knowing the milling rate under the processing conditions and controlling the duration of milling, etc.) at 1130.

At 1135, if the predefined depth of milling has been reached, the end-target of the process is completed, and the process ends at 1160. If the predefined depth of milling has not been reached, the ion milling process continues interactively at 1130.

At 1145, if the predefined length of time has passed, the end-target of the process is completed, and the process ends at 1160. If the predefined length of time has not passed, the ion milling process continues interactively at 1130.

At 1155, if the image of interest has been obtained, the end-target of the process is completed, and the process ends at 1160. If the image of interest has not been obtained, the ion milling process continues interactively at 1130.

Exemplary Software

The present apparatus can be operated, calibrated and/or controlled by a dedicated and integrated software package. Thus, the present disclosure also includes algorithms, computer program(s), computer-readable media and/or software, implementable and/or executable in a general purpose computer or workstation equipped with a conventional digital signal processor, and configured to perform one or more of the methods and/or one or more operations of the hardware disclosed herein. For example, the computer program or computer-readable medium generally contains a set of instructions which, when executed by an appropriate processing device (e.g., a signal processing device, such as a microcontroller, microprocessor or DSP device), is configured to perform the above-described method(s), operation(s), and/or algorithm(s).

The computer-readable medium may comprise any medium that can be read by a signal processing device configured to read the medium and execute code stored thereon or therein, such as a floppy disk, CD-ROM, magnetic tape or hard disk drive. Such code may comprise object code, source code and/or binary code. The code is generally digital, and is generally configured for processing by a conventional digital data processor (e.g., a microprocessor, microcontroller, or logic circuit such as a programmable gate array, programmable logic circuit/device or application-specific integrated circuit [ASIC]).

Thus, an aspect of the present invention relates to a non-transitory computer-readable medium, comprising a set of instructions encoded thereon adapted to change a position of a stationary specimen holder in any of three orthogonal linear directions and/or an angular direction; horizontally rotate rotatable ion optics, the rotatable ion optics being configured to direct an ion beam along either of two paths at a predetermined location on a specimen in the stationary specimen holder; select one of the two paths to focus and direct the ion beam at the predetermined location on the specimen, wherein the two paths are at angles relative to an exposed surface of the specimen that differ by at least 10°; generate the ion beam with an ion source; focus the ion beam onto the predetermined location on the specimen; and generate an image of the specimen including the predetermined location using an imaging device. In some embodiments, the set of instructions may be further adapted to select one of a plurality of ion sources for generating the ion beam.

Figure 20:
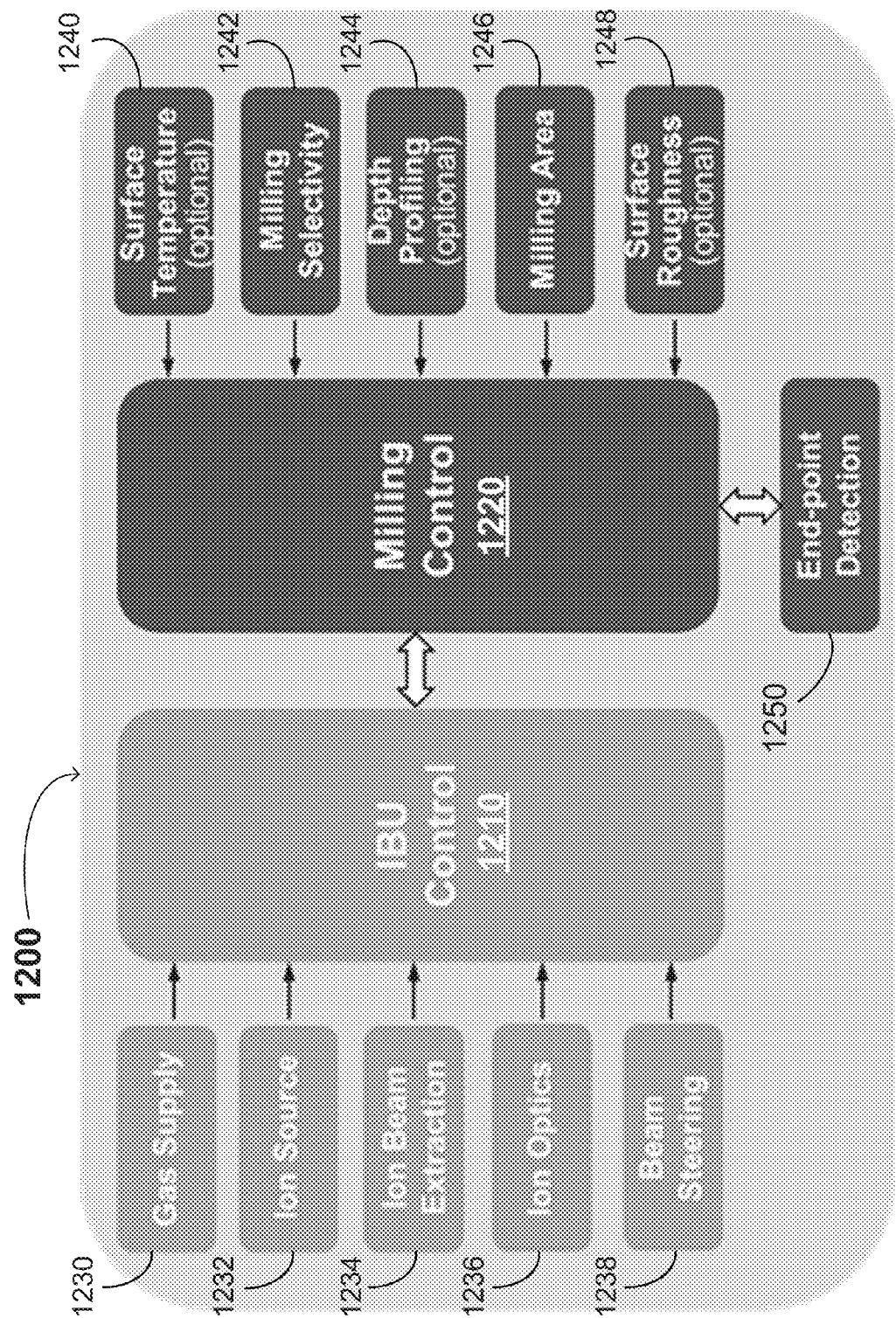
FIG. 20 is a block diagram for exemplary process control in accordance with one or more embodiments of the present invention.

FIG. 20 is a block diagram 1200 for exemplary process control in accordance with one or more embodiments of the present invention. The present invention thus provides real-time computer process control of milling depth, planarity and roughness during ion beam micromachining using computer software.

Ion beam unit (IBU) control block 1210 controls the ion source selection and rotatable ion optics in the present system and/or apparatus. Block 1230 allows the user to select a gas supply and optionally other gas supply parameters (e.g., flow rate) for the chamber(s) housing the rotatable ion optics and/or the specimen. When the apparatus includes more than one ion source, block 1232 allows the user to select the ion source. Block 1234 allows the user to select parameters for ion beam extraction, such as beam energy, beam current, etc. Block 1236 allows the user to select parameters for the ion optics, such as the ion beam path and the degree or extent of rotation of the ion optics. Block 1238 allows the user to select parameters for beam steering, such as the X, Y and Z coordinates and the tilt angle of the specimen holder.

Milling control block 1220 allows the user to select or control particular parameters and/or limits of the milling process. For example, the user can control milling selectivity at block 1242, and define the area of the specimen to be milled at 1246. Optionally, when the apparatus includes a thermal imaging device or system, the user can limit the surface temperature at block 1240. When the apparatus includes a mechanism for determining the depth into which the specimen has been milled, the user can control and/or limit using block 1244 the depth to which the specimen is milled and/or the profile of the hole, opening or other cut into the specimen made by the apparatus. When the apparatus includes appropriate imaging equipment and/or profiling instrument(s), the user can control and/or limit using block 1248 the surface roughness of the specimen during milling. The milling control block 1220 also controls detection of the end-point of the milling process at 1250 based on defined end-point parameter definitions set by the user.

Thus, in further embodiments, the present apparatus may further comprise a general purpose computer or work station, equipped with a monitor, keyboard, mouse/trackball or other cursor-manipulating device, and configured to execute the exemplary software described with reference to FIG. 20. For safety purposes, the present apparatus may include a separate ON/OFF button (e.g., separate from the general purpose computer or work station) and/or emergency shut-off button.

CONCLUSION/SUMMARY

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:
1. An apparatus, comprising:
 a) a specimen holder, configured to hold a specimen in a stationary position;
 b) a table, configured to change the stationary position of the specimen holder in any of three orthogonal linear directions and an angular direction;
 c) one or more ion sources;

d) rotatable ion optics, configured to emit an ion beam towards a predetermined location on the specimen from any of the one or more ion sources at any angle around an axis orthogonal to a horizontal surface of the table while the specimen holder and the specimen are stationary;

e) a motor configured to rotate the ion optics; and f) an imaging device, configured to generate an image of the specimen including the predetermined location simultaneously with the rotatable ion optics emitting the ion beam.

2. The apparatus of claim 1, wherein the table includes a first mechanism to move the sample holder in a lateral direction, a second mechanism to move the sample holder in a longitudinal direction, a third mechanism to move the sample holder in a vertical direction, and a fourth mechanism to move the sample holder in the angular direction, the angular direction being defined by an axis in a plane defined by the lateral and longitudinal directions.

3. The apparatus of claim 1, wherein the imaging device comprises an optical camera, a microscope, and/or a thermovision device.

4. The apparatus of claim 1, further comprising a laser configured to irradiate the predetermined location with a predetermined dose of radiation.

5. The apparatus of claim 1, further comprising a laser interferometer configured to determine a depth of ion milling into the specimen at the predetermined location.

6. The apparatus of claim 1, further comprising a vacuum chamber configured to sealingly house at least the specimen holder and the ion optics.

7. The apparatus of claim 1, wherein the imaging device comprises a microscope or an interferometer that measures a milling depth at the predetermined location.

8. The apparatus of claim 1, wherein the one or more ion sources includes a first ion source and a second ion source different from the first ion source.

9. The apparatus of claim 8, wherein the first ion source is selected from the group consisting of noble gas ion sources and the second ion source is selected from the group consisting of Group 3, Group 4 and Group 5 ion sources.

10. The apparatus of claim 8, wherein the first ion source comprises a duoplasmatron and the second ion source comprises a liquid metal ion source or a cluster ion source.

11. The apparatus of claim 1, wherein the ion optics comprises (i) a first ion path configured to emit the ion beam at a first angle relative to an exposed surface of the specimen and (ii) a second ion path configured to emit the ion beam at a second angle relative to the exposed surface of the specimen, the first and second angles differing by at least 10°.

12. The apparatus of claim 11, wherein the ion optics focuses the ion beam in each of the first and second ion paths onto the predetermined location on the specimen.

13. The apparatus of claim 11, wherein the one or more ion sources and the imaging device are on a same side of the specimen holder and the table.

14. The apparatus of claim 11, wherein the first and second angles differ by at least 35°.

15. The apparatus of claim 11, wherein the ion optics further comprises a first matching lens configured to focus the ion beam from the one or more ion sources, and a bidirectional deflector configured to direct the ion beam to either the first ion path or the second ion path.

16. The apparatus of claim 15, wherein the ion optics further comprises a first deflector receiving the ion beam from the one or more ion sources, and a beam current monitor configured to determine a beam current of the ion beam.

17. The apparatus of claim 15, wherein the first ion path comprises a beam stigmator, an objective lens, and a beam scanning plate, and the second ion path comprises a second matching lens, a second beam deflector, and a quadrupole beam aligner.

18. An apparatus, comprising:

a) a specimen holder, configured to hold a specimen in a stationary position;

b) a table, configured to change the stationary position of the specimen holder in any of three orthogonal linear directions and an angular direction;

c) one or more ion sources;

d) rotatable ion optics, configured to emit an ion beam towards a predetermined location on the specimen from any of the one or more ion sources at any angle around an axis orthogonal to a horizontal surface of the table, the rotatable ion optics comprising (i) a first ion path configured to emit the ion beam at a first angle relative to an exposed surface of the specimen, the first ion path comprising a beam stigmator, an objective lens, and a beam scanning plate, (ii) a second ion path configured to emit the ion beam at a second angle relative to the exposed surface of the specimen, the first and second angles differing by at least 10°, the second ion path comprising a second matching lens, a second beam deflector, and a quadrupole beam aligner, (iii) a first matching lens configured to focus the ion beam from the one or more ion sources, and (iv) a bidirectional deflector configured to direct the ion beam to either the first ion path or the second ion path; and e) an imaging device, configured to generate an image of the specimen including the predetermined location simultaneously.

19. The apparatus of claim 18, further comprising a motor configured to rotate the ion optics.

20. The apparatus of claim 18, wherein the one or more ion sources includes a first ion source and a second ion source different from the first ion source.

21. The apparatus of claim 20, wherein the first ion source is selected from the group consisting of noble gas ion sources and the second ion source is selected from the group consisting of Group 3, Group 4 and Group 5 ion sources.

22. An apparatus, comprising:

a) a specimen holder, configured to hold a specimen in a stationary position;

b) a table, configured to change the stationary position of the specimen holder in any of three orthogonal linear directions and an angular direction;

c) a first ion source;

d) a second ion source different from the first ion source;

e) rotatable ion optics, configured to emit an ion beam towards a predetermined location on the specimen from any of the one or more ion sources at any angle around an axis orthogonal to a horizontal surface of the table while the specimen holder and the specimen are stationary, wherein ion beams from each of the first and second ion sources are configured to travel along a same path in the rotatable ion optics; and f) an imaging device, configured to generate an image of the specimen including the predetermined location simultaneously with the rotatable ion optics emitting the ion beam.

23. The apparatus of claim 22, wherein the first ion source comprises a duoplasmatron and the second ion source comprises a liquid metal ion source or a cluster ion source.

24. The apparatus of claim 22, wherein the first ion source is selected from the group consisting of noble gas ion sources and the second ion source is selected from the group consisting of Group 3, Group 4 and Group 5 ion sources.

* * * * *